United States Patent
Gregersen et al.

(10) Patent No.: US 11,039,933 B2
(45) Date of Patent: Jun. 22, 2021

(54) INTERBODY SPINAL FUSION IMPLANT WITH SUPPORT STRUTS

(71) Applicant: Innovasis, Inc., Salt Lake City, UT (US)

(72) Inventors: Colin S. Gregersen, Salt Lake City, UT (US); Brandon Walker, Layton, UT (US)

(73) Assignee: Innovasis, Inc., Salt Lake City, UT (US)

( * ) Notice: Subject to any disclaimer, the term of this patent is extended or adjusted under 35 U.S.C. 154(b) by 177 days.

(21) Appl. No.: 15/844,141

(22) Filed: Dec. 15, 2017

(65) Prior Publication Data

US 2019/0183653 A1    Jun. 20, 2019

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2002/3008* (2013.01); *A61F 2002/3092* (2013.01); *A61F 2002/30156* (2013.01); *A61F 2002/30205* (2013.01); *A61F 2002/30593* (2013.01); *A61F 2002/30774* (2013.01); *A61F 2002/30784* (2013.01); *A61F 2002/30891* (2013.01)

(58) Field of Classification Search
CPC ............ A61F 2/4455; A61F 2002/4475; A61F 2/442; A61F 2002/4445; A61F 2002/445; A61F 2/30767; A61F 2/30771; A61F 2002/30772; A61F 2002/30784; A61F 2002/30785; A61F 2002/30787; A61F 2002/30789; A61F 2002/3092
USPC ..................... 606/246–249; 623/17.11–17.16
See application file for complete search history.

(56) References Cited

U.S. PATENT DOCUMENTS

| | | | |
|---|---|---|---|
| 5,888,223 A | 5/1999 | Bray, Jr. | |
| 8,430,930 B2 | 4/2013 | Hunt | |
| 2007/0255414 A1* | 11/2007 | Melkent | A61F 2/30744 623/17.16 |
| 2010/0161061 A1* | 6/2010 | Hunt | A61F 2/2846 623/17.16 |
| 2013/0116793 A1 | 5/2013 | Kloss | |
| 2014/0288650 A1 | 9/2014 | Hunt | |
| 2015/0018956 A1 | 1/2015 | Steinmann et al. | |
| 2016/0022431 A1 | 1/2016 | Wickham | |
| 2016/0199193 A1 | 7/2016 | Willis et al. | |
| 2016/0213485 A1 | 7/2016 | Schaufler et al. | |
| 2016/0213486 A1 | 7/2016 | Nunley et al. | |
| 2016/0213488 A1 | 7/2016 | Moore et al. | |
| 2017/0156880 A1* | 6/2017 | Halverson | A61F 2/0077 |

* cited by examiner

*Primary Examiner* — Eduardo C Robert
*Assistant Examiner* — Christina Negrellirodriguez
(74) *Attorney, Agent, or Firm* — Workman Nydegger

(57) ABSTRACT

An interbody spinal fusion implant includes a top wall, a bottom wall that is spaced apart from the top wall so that a cavity is formed therebetween, and a sidewall extending between the top wall and the bottom wall. At least a portion of the sidewall includes: a row of a plurality of spaced apart outer struts extending between the top wall and the bottom wall, and a row of a plurality of spaced apart inner struts extending between the top wall and the bottom wall, the row of inner struts being set back a distance from the row of outer struts toward the cavity.

27 Claims, 16 Drawing Sheets

INTERBODY SPINAL FUSION IMPLANT WITH SUPPORT STRUTS

CROSS-REFERENCE TO RELATED APPLICATIONS

Not applicable.

BACKGROUND OF THE INVENTION

1. The Field of the Invention

The present invention relates to interbody spinal fusion implants for use in fusing together adjacent vertebrae.

2. The Relevant Technology

The spinal column is made up of spaced apart vertebrae that are each separated by a cushioning disc. If a disc ruptures or is otherwise damaged, the adjacent vertebrae can press against the spinal cord which can cause pain and loss of mobility. In one approach to treating a damaged disc, at least a portion of the damaged disc is removed and an interbody spinal fusion implant is inserted between the adjacent vertebrae. The implant keeps the vertebrae separated to prevent the vertebrae from pressing on the spinal cord. Eventually, bone grows between the adjacent vertebrae by passing through and/or around the fusion implant so as to fuse the adjacent vertebrae together, thereby precluding any movement between the vertebrae. The above same procedure can be used for fusing together vertebrae where the vertebrae have been damaged or are deformed. For example, vertebrae are commonly fused together as part of a procedure for treating scoliosis.

To help facilitate bone growth between the vertebrae, the fusion implant is commonly formed with a hollow cavity that is manually filled with a bone growth material prior to insertion of the fusion implant between the vertebrae. Openings are also commonly formed on the fusion implant to enable the bone to grow through the fusion implant.

One of the shortcomings of conventional fusion implants is that due to the structural reinforcement needed to prevent collapse of the fusion implant when it is placed between adjacent vertebrae, the openings extending through the implant are typically very small. Because of the small openings, it can be difficult for bone to grow quickly and uniformly through the implant. In other embodiments, larger openings are formed through the fusion implant. However, to compensate for these larger openings, more supports structures are formed throughout the fusion implant extending between the upper and lower surfaces. As a result, the cavity within the implant that is used for receiving bone growth material is either eliminated or is substantially reduced. Likewise, the support members can obstruct, limit or at least complicating the packing of bone growth material into the cavity. Reducing the amount of bone growth material that can be used within a fusion implant again slows the rate of bone growth through the fusion implant and thus slows patient recovery time.

Accordingly, what is needed in the art are interbody spinal fusion implants that solve one or more of the problems of conventional interbody spinal fusion implants. For example, it would be desirable to have interbody spinal fusion implants that achieve improved bone growth laterally and/or vertically through the fusion implant. It would also be desirable to have fusion implants that maximize the size of the cavity within the fusion implant without sacrificing needed strength properties and without obstructing access to the cavity.

SUMMARY OF THE INVENTION

In a first independent aspect of the present invention, an interbody spinal fusion implant includes:
  a top wall;
  a bottom wall that is spaced apart from the top wall so that a cavity is formed therebetween;
  a sidewall extending between the top wall and the bottom wall, at least a portion of the sidewall comprising:
    a row of a plurality of spaced apart outer struts extending between the top wall and the bottom wall;
    a row of a plurality of spaced apart inner struts extending between the top wall and the bottom wall, the row of inner struts being set back a distance from the row of outer struts toward the cavity.

In one embodiment the inner struts are staggered relative to the outer struts so that each inner strut is disposed between an adjacent pair of outer struts when the row of outer struts are viewed in a front elevational view.

In another embodiment each inner strut is centrally disposed between an adjacent pair of outer struts when the row of outer struts are viewed in a front elevational view.

In another embodiment each inner strut and the adjacent pair of outer struts each partially bound an open channel having a triangular cross section that extends between the top wall and the bottom wall.

In another embodiment each inner strut and the adjacent pair of outer struts are located at corners of the open channel having the triangular cross section that extends between the top wall and the bottom wall.

In another embodiment the interbody spinal fusion implant can further include:
  the outer struts being linear and disposed in parallel alignment; and
  the inner struts being linear and disposed in parallel alignment.

In another embodiment the outer struts are disposed parallel to the inner struts.

In another embodiment the row of inner struts is linear and the row of outer struts is linear.

In another embodiment the outer struts are angle relative to the inner struts so that the outer struts and the inner struts are not disposed in parallel alignment.

In another embodiment the plurality of outer struts comprise a first outer strut and a spaced apart second outer strut, the first outer strut being angled relative to the second outer strut so that the first outer strut and the second outer strut are not disposed in parallel alignment.

In another embodiment the interbody spinal fusion implant can further include:
  the plurality of outer struts comprising at least six outer struts; and
  the plurality of inner struts comprising at least six inner struts.

In another embodiment the interbody spinal fusion implant can further include a support member extending between one of the plurality of outer struts and one of the plurality of inner struts.

In another embodiment the support member connects with the one of the plurality of outer struts so as to form an angle therebetween in a range between 30° and 90°.

In another embodiment each outer strut has a circular, elliptical, or polygonal transverse cross section.

In another embodiment the inner struts are spaced apart from and do not directly connect to the outer struts.

In a second independent aspect of the present invention, an interbody spinal fusion implant includes:
- a top wall;
- a bottom wall that is spaced apart from the top wall so that a cavity is formed therebetween;
- a sidewall extending between the top wall and the bottom wall, at least a portion of the sidewall comprising:
  - a row of a plurality of spaced apart outer struts extending between the top wall and the bottom wall;
  - a row of a plurality of spaced apart inner struts extending between the top wall and the bottom wall, the row of inner struts being set back a distance from the row of outer struts toward the cavity; and
  - a first support member that extends between a select one of the outer struts and a select one of the inner struts without directly contacting to the top wall or the bottom wall.

In one embodiment the first support member connects with the select one of the outer struts or the select one of the inner struts so as to form an angle therebetween in a range between 30° and 60°.

In another embodiment the first support member connects with the select one of the outer struts or the select one of the inner struts so as to form an angle therebetween in a range between 60° and 90°.

In another embodiment the first support member has a circular, elliptical, or polygonal transverse cross section.

In another embodiment comprising a second support that extends between the select one of the outer struts and the select one of the inner struts without directly contacting to the top wall or the bottom wall, the second support member having a different orientation than the first support member.

In another embodiment the inner struts and the outer struts each have a maximum diameter and the first support member has a maximum diameter, the maximum diameter of the first support member being smaller than the maximum diameter of the inner struts and the outer struts.

In another embodiment the interbody spinal fusion implant can further include:
- the outer struts being linear and disposed in parallel alignment; and
- the inner struts being linear and disposed in parallel alignment.

In another embodiment the outer struts are angle relative to the inner struts so that the outer struts and the inner struts are not disposed in parallel alignment.

In another embodiment the plurality of outer struts comprise a first outer strut and a spaced apart second outer strut, the first outer strut being angled relative to the second outer strut so that the first outer strut and the second outer strut are not disposed in parallel alignment.

In a third independent aspect of the present invention, an interbody spinal fusion implant includes:
- a top wall comprising a top outer perimeter rail, a top inner perimeter rail that bounds a top access, and a top grating that extends from the top outer perimeter rail to the top inner perimeter rail;
- a bottom wall that is spaced apart from the top wall, the bottom wall comprising a bottom outer perimeter rail, a bottom inner perimeter rail that bounds a bottom access, and a bottom grating that extends from the bottom outer perimeter rail to the bottom inner perimeter rail; and
- a sidewall extending between the top wall and the bottom wall, at least a portion of the sidewall comprising:
  - a row of a plurality of spaced apart outer struts extending between the top outer perimeter rail and the bottom outer perimeter rail; and
  - a row of a plurality of spaced apart inner struts extending between the top outer perimeter rail and the bottom outer perimeter rail, the row of inner struts being set back a distance from the row of outer struts toward the top access and the bottom access.

In one embodiment the upper grating comprises a network of interconnected rods that bound a plurality of openings.

In another embodiment the network of interconnected rods are disposed in a uniform pattern.

In another embodiment the network of interconnected rods are disposed in a common plane.

In another embodiment the rod of the network of interconnected rods interconnect at right angles In another embodiment the inner struts do not directly connect to the top grating or the bottom grating.

In a fourth independent aspect of the present invention, an interbody spinal fusion implant includes:
- a top wall;
- a bottom wall that is spaced apart from the top wall so that a cavity is formed therebetween, the bottom wall comprising:
  - a bottom outer perimeter rail;
  - a bottom inner perimeter rail that bounds a bottom access, the bottom access communicating with the cavity; and
  - a bottom grating that extends from the bottom outer perimeter rail to the bottom inner perimeter rail, the bottom grating comprising a network of interconnected rods that join together at junction nodes and that bound a plurality of openings that communicate with the cavity, each junction node having a bottom surface that faces toward the cavity, the bottom surface of a plurality of the junction nodes being freely exposed; and
- a sidewall extending between the top wall and the bottom wall, at least a portion of the sidewall comprising a plurality of spaced apart struts extending between the top outer perimeter rail and the bottom outer perimeter rail.

In one embodiment the network of interconnected rods are disposed in a uniform pattern.

In another embodiment the top wall includes:
- a top outer perimeter rail;
- a top inner perimeter rail that bounds a top access, the top access communicating with the cavity; and
- a top grating that extends from the top outer perimeter rail to the top inner perimeter rail, the top grating comprising a network of interconnected rods that join together at junction nodes and that bound a plurality of openings that communicate with the cavity, each junction node having a bottom surface that faces toward the cavity, the bottom surface of a plurality of the junction nodes of the top grating being freely exposed.

In another embodiment the open cavity extends between the bottom surface of the plurality of the junction nodes of the bottom grating and the bottom surface of the plurality of the junction nodes of the top grating.

In another embodiment the plurality of spaced apart struts comprise a row of a plurality of spaced apart outer struts extending between the top wall and the bottom wall.

In another embodiment the plurality of spaced apart struts further comprise a row of a plurality of spaced apart inner struts extending between the top wall and the bottom wall, the row of inner struts being set back a distance from the row of outer struts toward the cavity.

In a fifth independent aspect of the present invention, an interbody spinal fusion implant includes:
a top wall;
a bottom wall that is spaced apart from the top wall so that a cavity is formed therebetween, the bottom wall comprising:
a bottom outer perimeter rail;
a bottom inner perimeter rail that bounds a bottom access, the bottom access communicating with the cavity; and
a bottom grating that extends from the bottom outer perimeter rail to the bottom inner perimeter rail, the bottom grating comprising a network of interconnected rods that join together at junction nodes and that bound a plurality of openings that communicate with the cavity, a plurality of the junction nodes of the bottom grating comprising a junction body and a tooth projecting from the junction body away from the cavity; and
a sidewall extending between the top wall and the bottom wall.

In one embodiment the junction body has a circular transverse cross section.

In another embodiment the tooth has a conical configuration.

In another embodiment at least a portion of the sidewall comprises a plurality of spaced apart struts extending between the top outer perimeter rail and the bottom outer perimeter rail.

In a sixth independent aspect of the present invention, an interbody spinal fusion implant comprising:
a top wall having a top outer perimeter rail, a top inner perimeter rail that bounds a top access, and an interior surface that extends between the top inner perimeter rail and the top outer perimeter rail; and
a bottom wall that is spaced apart from the top wall so that a cavity is formed therebetween, the bottom wall comprising a bottom outer perimeter rail, a bottom inner perimeter rail that bounds a bottom access, and an interior surface that extends between the bottom inner perimeter rail and the bottom outer perimeter rail, the top access and the bottom access communicating with the cavity, at least a portion of the cavity extending between interior surface of the top wall and the interior surface of the bottom wall; and
a sidewall extending between the top wall and the bottom wall, at least a portion of the sidewall comprising a plurality of spaced apart struts extending between the top outer perimeter rail and the bottom outer perimeter rail.

In one embodiment the top wall comprises a top grating that extends from the top outer perimeter rail to the top inner perimeter rail, the top grating comprising a network of interconnected rods that join together at junction nodes and that bound a plurality of openings that communicate with the cavity.

Each of the above independent aspects of the invention may include any of the features, options and possibilities set out elsewhere in this document, including those included in each of the above aspects.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
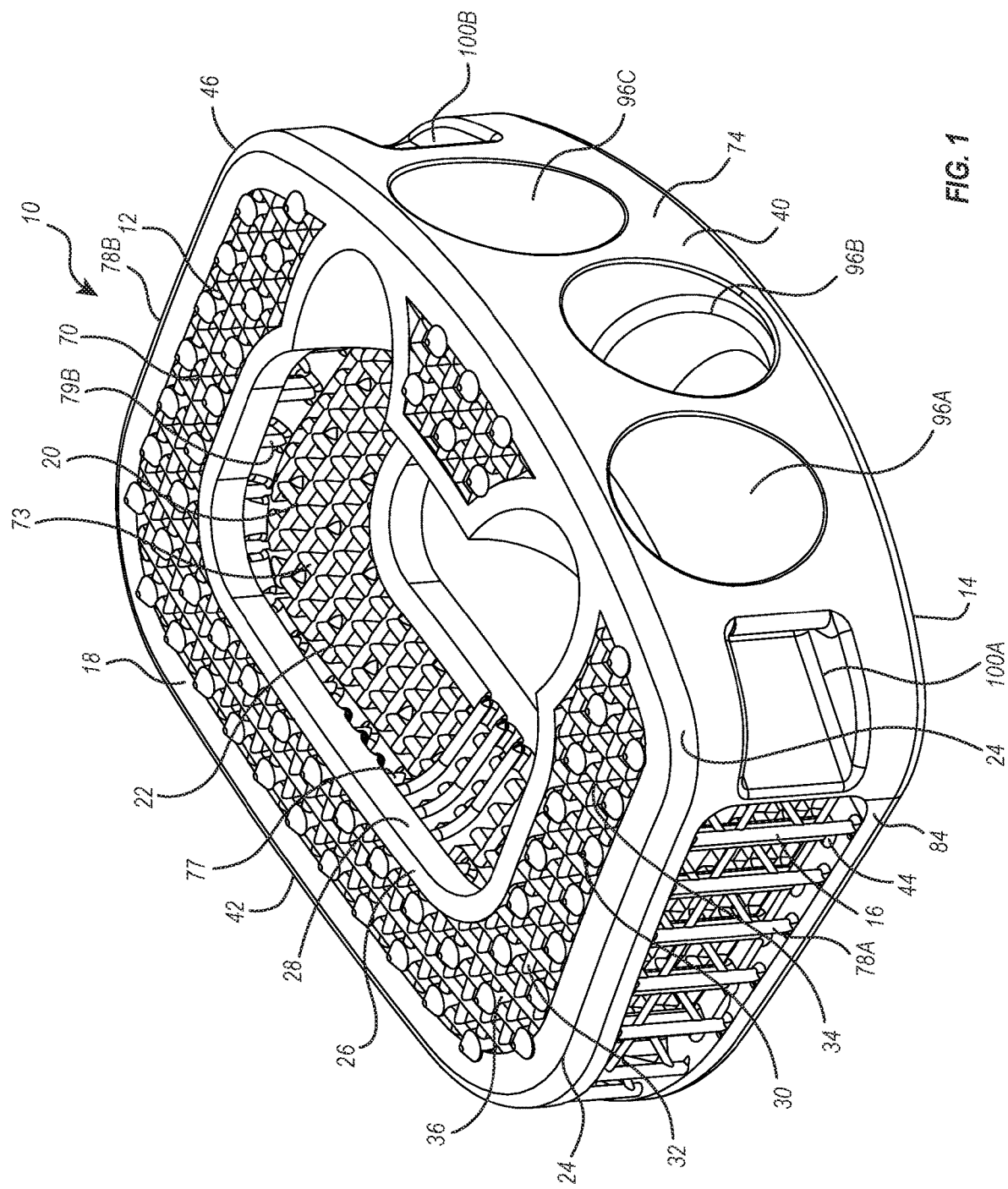
FIG. 1 is a top, front perspective view of an interbody spinal fusion implant of the present invention.

Before describing the present disclosure in detail, it is to be understood that this disclosure is not limited to parameters of the particularly exemplified systems, methods, apparatus, products, processes, compositions, and/or kits, which may, of course, vary. It is also to be understood that the terminology used herein is only for the purpose of describing particular embodiments of the present disclosure, and is not necessarily intended to limit the scope of the disclosure in any particular manner. Thus, while the present disclosure will be described in detail with reference to specific embodiments, features, aspects, configurations, etc., the descriptions are illustrative and are not to be construed as limiting the scope of the claimed invention. Various modifications can be made to the illustrated embodiments, features, aspects, configurations, etc. without departing from the spirit and scope of the invention as defined by the claims. Thus, while various aspects and embodiments have been disclosed herein, other aspects and embodiments are contemplated.

Unless defined otherwise, all technical and scientific terms used herein have the same meaning as commonly understood by one of ordinary skill in the art to which the present disclosure pertains. While a number of methods and apparatus similar or equivalent to those described herein can be used in the practice of the present disclosure, only certain exemplary methods and apparatus are described herein.

Various aspects of the present disclosure, including devices, systems, methods, etc., may be illustrated with reference to one or more exemplary embodiments or implementations. As used herein, the terms "embodiment," "alternative embodiment" and/or "exemplary implementation" means "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to a "strut" includes one, two, or more struts.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including in the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct connection between two components or, where appropriate, an indirect connection to one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured to one another. For instance, coupling, attaching, connecting, and/or joining can comprise placing, positioning, and/or disposing the components together or otherwise adjacent in some implementations.

As used herein, directional and/or arbitrary terms, such as "top," "bottom," "front," "back," "left," "right," "up," "down," "upper," "lower," "inner," "outer," "internal," "external," "interior," "exterior," "proximal," "distal" and the like can be used solely to indicate relative directions and/or orientations and may not otherwise be intended to limit the scope of the disclosure, including the specification, invention, and/or claims.

Where possible, like numbering of elements have been used in various figures. In addition, similar elements and/or elements having similar functions may be designated by similar numbering (e.g., element "10" and element "10'.") Furthermore, alternative configurations of a particular element may each include separate letters or other symbol appended to the element number. Accordingly, an appended letter or symbol can be used to designate an alternative design, structure, function, implementation, and/or embodiment of an element or feature without an appended letter or symbol. Similarly, multiple instances of an element and or sub-elements of a parent element may each include separate letters or symbols appended to the element number. In each case, the element label may be used without an appended letter or symbol to generally refer to instances of the element or any one of the alternative elements. Element labels including an appended letter or symbol can be used to refer to a specific instance of the element or to distinguish or draw attention to multiple uses of the element. However, element labels including an appended letter or symbol are not meant to be limited to the specific and/or particular embodiment(s) in which they are illustrated. In other words, reference to a specific feature in relation to one embodiment should not be construed as being limited to applications only within said embodiment.

It will also be appreciated that where a range of values (e.g., less than, greater than, at least, and/or up to a certain value, and/or between two recited values) is disclosed or recited, any specific value or range of values falling within the disclosed range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

It is also noted that systems, methods, apparatus, devices, products, processes, compositions, and/or kits, etc., according to certain embodiments of the present invention may include, incorporate, or otherwise comprise properties, features, aspects, steps, components, members, and/or elements described in other embodiments disclosed and/or described herein. Thus, reference to a specific feature, aspect, steps, component, member, element, etc. in relation to one embodiment should not be construed as being limited to applications only within said embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims. To facilitate understanding, like reference numerals have been used, where possible, to designate like elements common to the figures.

The present invention relates to interbody spinal fusion implants for use in fusing together adjacent vertebra. The fusion implants of the present invention can have a variety of different configurations and can be designed for different surgeries and for use at different locations on the spine. For example, and not by limitation, the fusion implants can comprise an anterior lumbar interbody fusion (ALIF) implant, a posterior lumbar interbody fusion (PLIF) implant, a transforaminal lumbar interbody fusion (TLIF) implant, a lateral lumbar interbody fusion (LLIF) implant, an anterior cervical discectomy and fusion (ACDF) implant, i.e., implants that are used in the foregoing surgeries. Other implants and applications are also applicable.

Figure 2:
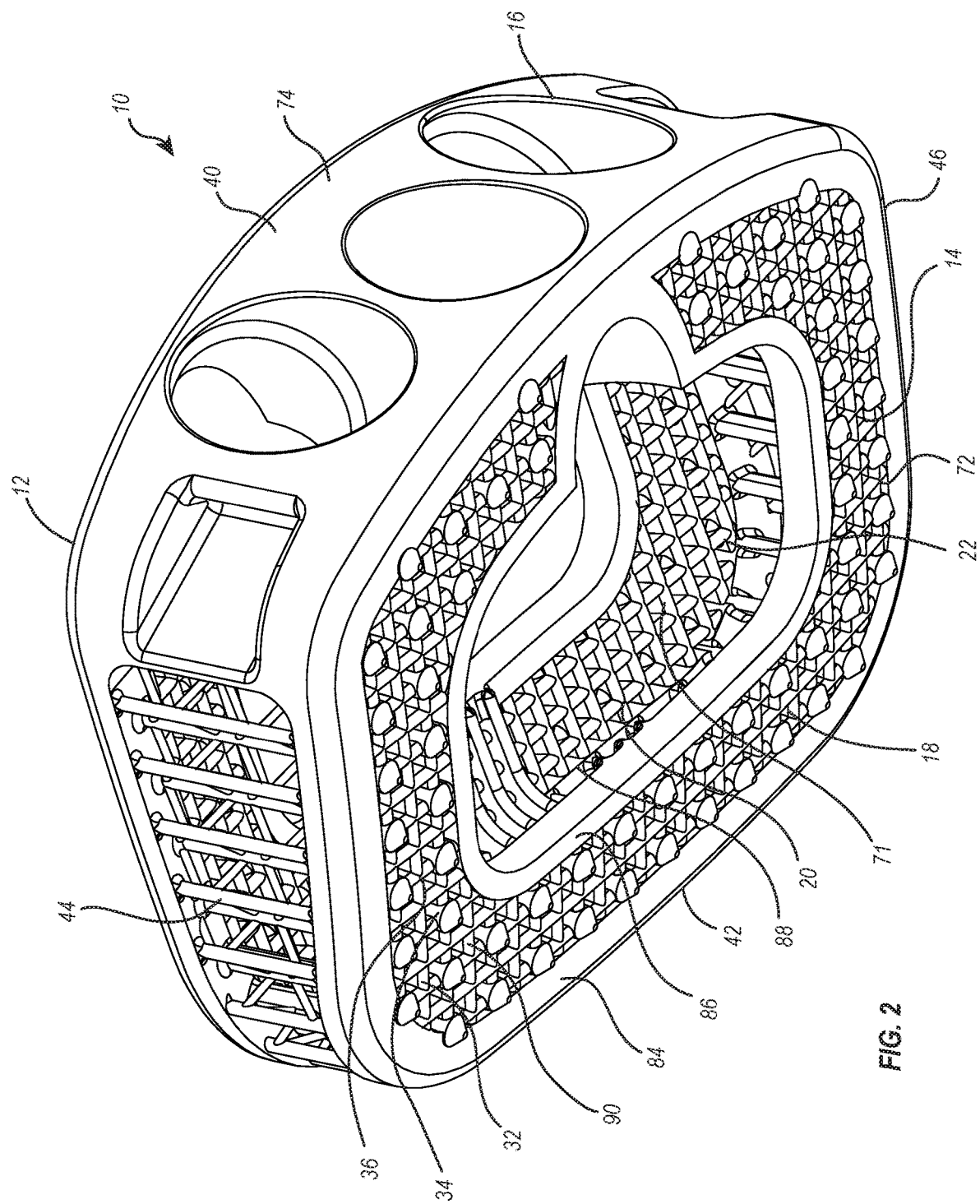
FIG. 2 is bottom, front perspective view of the fusion implant shown in FIG. 1.
Figure 3:
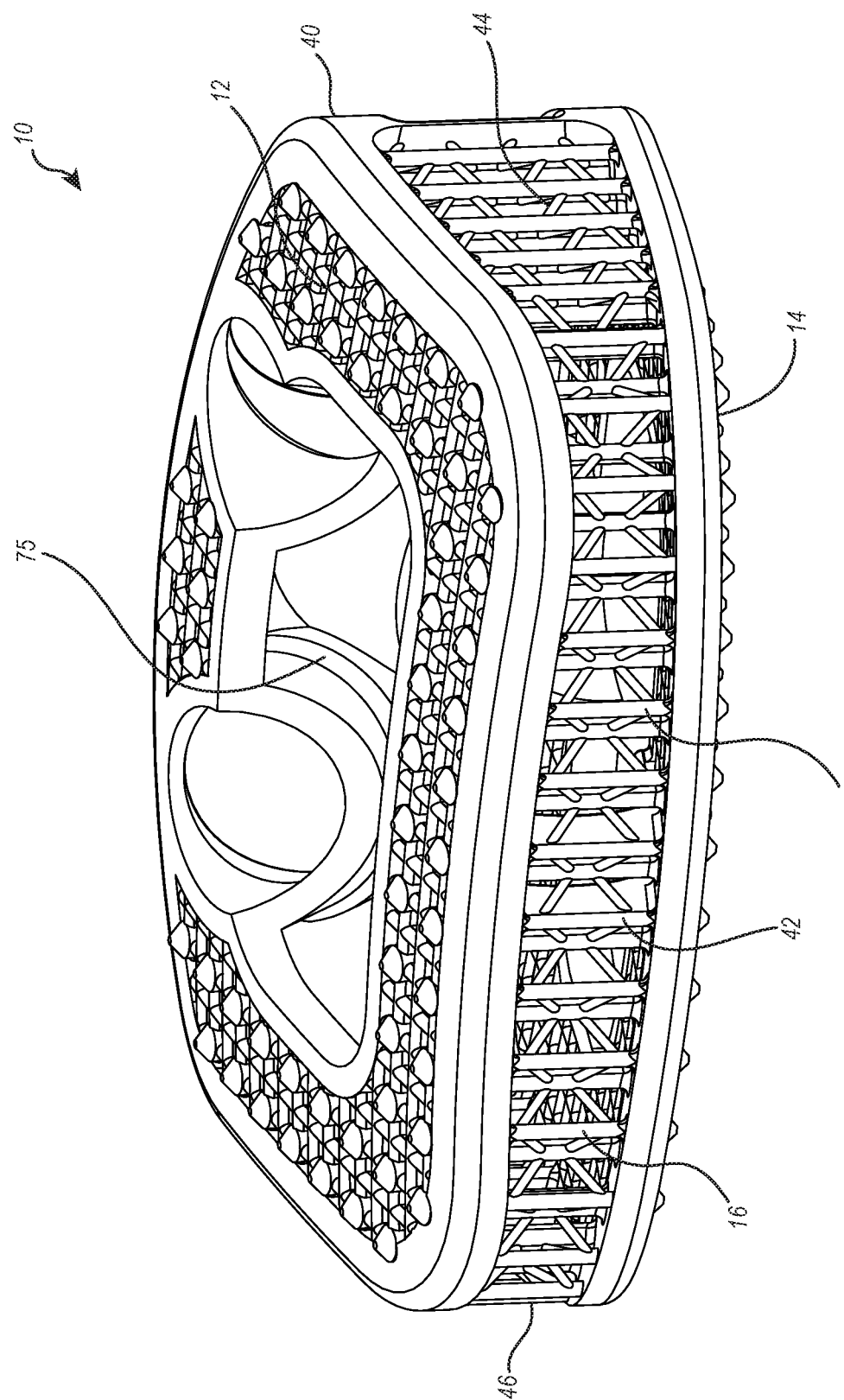
FIG. 3 is top, back perspective view of the fusion implant shown in FIG. 1.

Depicted in FIGS. 1 and 2 is one embodiment of an inventive interbody spinal fusion implant 10 incorporating features of the present invention. In general, fusion implant 10 comprises a top wall 12, a spaced apart bottom wall 14 and an encircling sidewall 16 extending therebetween. Encircling sidewall 16 includes a front wall 40, a back wall 42 (FIG. 3), and opposing side walls 44 and 46 that extend between walls 40 and 42. For reference purposes, fusion implant 10 has a vertical direction extending between top wall 12 and opposing bottom wall 14 and a horizontal or lateral direction extending between opposing side walls 44 and 46. Continuing with FIGS. 1 and 2, fusion implant 10 has an exterior surface 18 and an interior surface 20. Interior surface 20 at least partially bounds a cavity 22 in which a bone growth material, such as bone allograft or autograft, can be packed during use of fusion implant 10.

Further regarding exterior surface 18 and interior surface 20, top wall 12 comprises an exterior top surface 70 and an opposing interior top surface 71; bottom wall 14 comprises an exterior bottom surface 72 and an opposing interior bottom surface 73; front wall 40 comprises an exterior front surface 74 and an opposing interior front surface 75 (FIG. 3); back wall 42 (FIG. 3) comprises an exterior back surface 76 and an opposing interior back surface 77, side wall 44 includes an exterior side surface 78A and an opposing interior side surface 79A (FIG. 5); and side wall 46 includes an exterior side surface 78B and an opposing interior side surface 79B. Fusion implant 10 is wedge-shaped with exterior top surface 70 and exterior bottom surface 72 inwardly tapering from front wall 40 to back wall 42. Exterior top surface 70 and exterior bottom surface 72 can be linear but typically have a slight convex arch or curve extending from front wall 40 to back wall 42. Fusion implant 10 can also be bi-convex with exterior top surface 70 and exterior bottom surface 72 also having slight convex arch or curve extending between opposing side walls 44 and 46.

Figure 12:
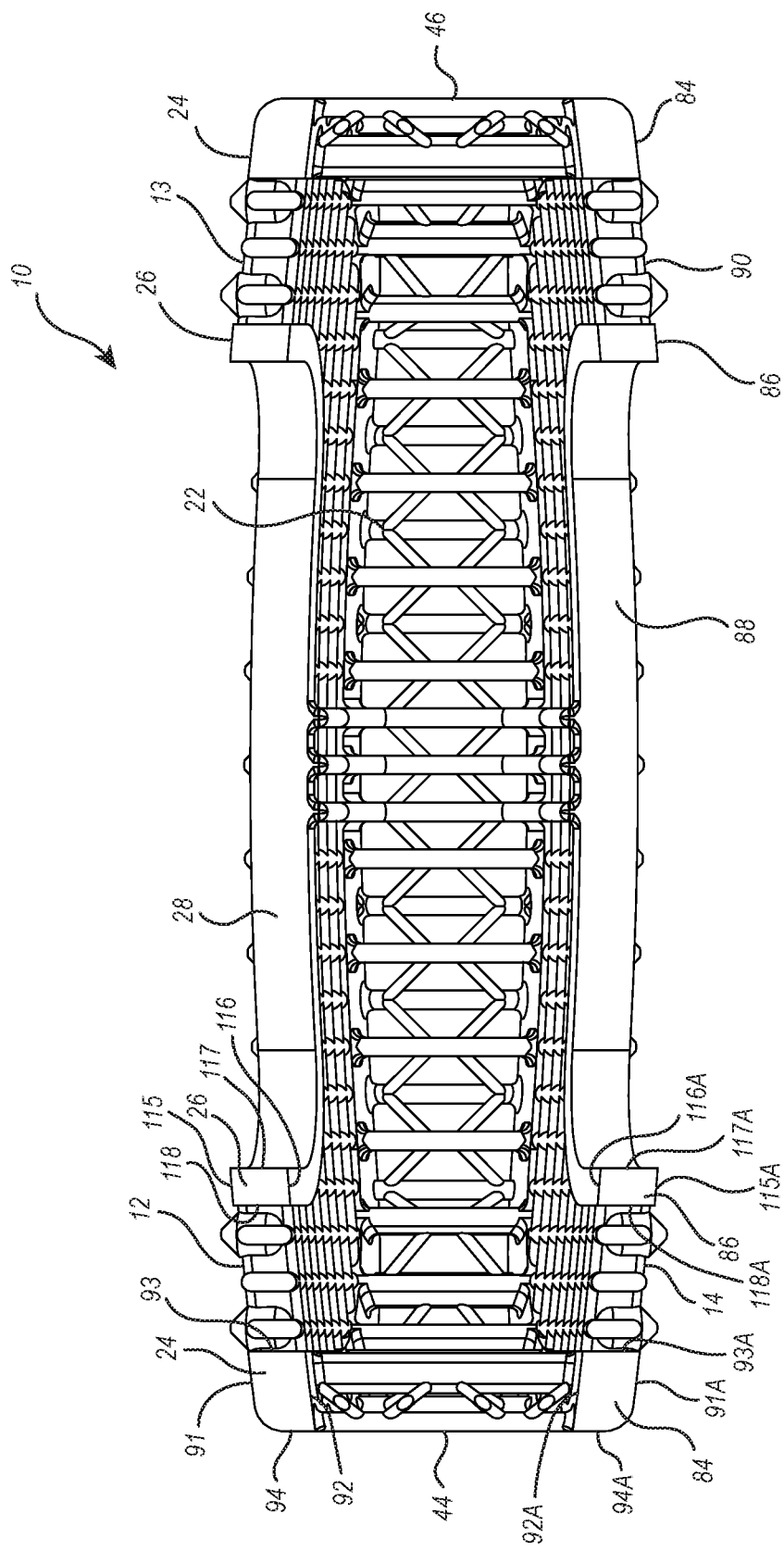
FIG. 12 is an elevated cross sectional view of the back portion of the fusion implant shown in FIG. 1.

Continuing with FIG. 1, top wall 12 includes a top outer perimeter rail 24 and a top inner perimeter rail 26. Top inner perimeter rail 26 is disposed radially inward from top outer perimeter rail 24 and bounds a top access 28 that communicates with cavity 22. With reference to FIG. 12, although not required, top outer perimeter rail 24 and top inner perimeter rail 26 are depicted as having a substantially rectangular transverse cross section. More specifically, top outer perimeter rail 24 has a top surface 91 and an opposing bottom surface 92 that extend between an interior surface 93 and an opposing exterior surface 94. Interior surface 93 faces toward top inner perimeter rail 26. Top inner perimeter rail 26 also has a top surface 115 and an opposing bottom surface 116 that extend between an interior surface 117 and an opposing exterior surface 118. Interior surface 117 bounds top access 28. Top outer perimeter rail 24 and top inner perimeter rail 26 both typically form a continuous loop and form a solid structural member. Top wall 12 also includes a top grating 30 that extends from the top outer perimeter rail 24 to top inner perimeter rail 26.

Figure 4:
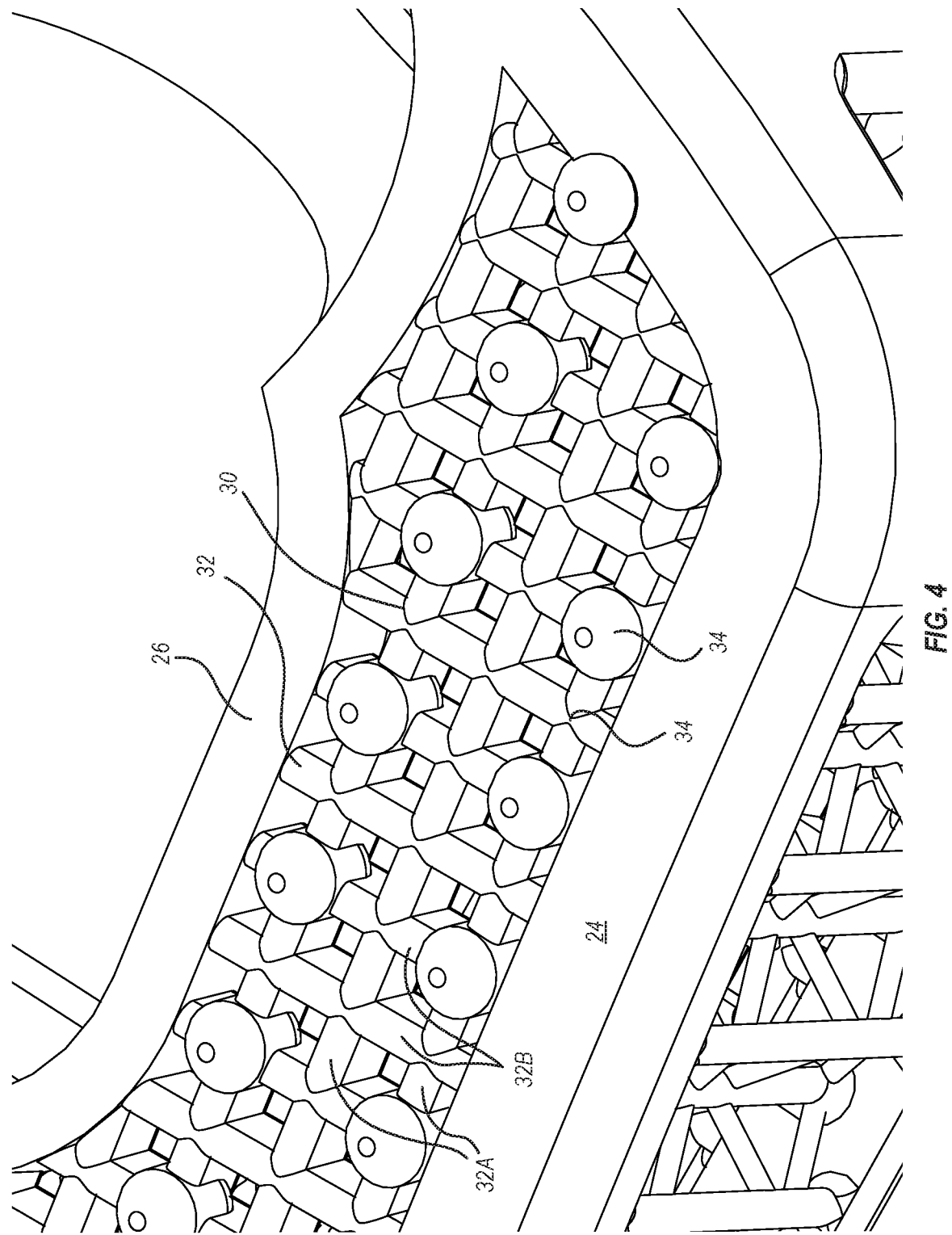
FIG. 4 is an enlarged top perspective view of the fusion implant shown in FIG. 1.

Returning to FIG. 1, top grating 30 comprises a network of interconnecting rods 32 that join together at junction nodes 34 and that bound a plurality of openings 36 that communicate with cavity 22. Interconnecting rods 32 are typically linear or have a slight curve and can be disposed to connect a right angles. For example, as more clearly depicted in FIG. 4, rods 32 can comprise first rods 32A and orthogonally disposed second rods 32B. First rods 32A are orientated so that the longitudinal axes thereof extend between front wall 40 and back wall 42 (FIG. 1) while second rods 32B are orientated so that the longitudinal axes thereof extend between side walls 44 and 46. In other embodiments, however, rods 32 can be disposed at different orientations and can intersect at different angles. For example, rods 32 could intersect at junction nodes 34 so that an inside angle is formed between rods 32 in a range between 60° to 30°. Other angles can also be used.

Figure 5:
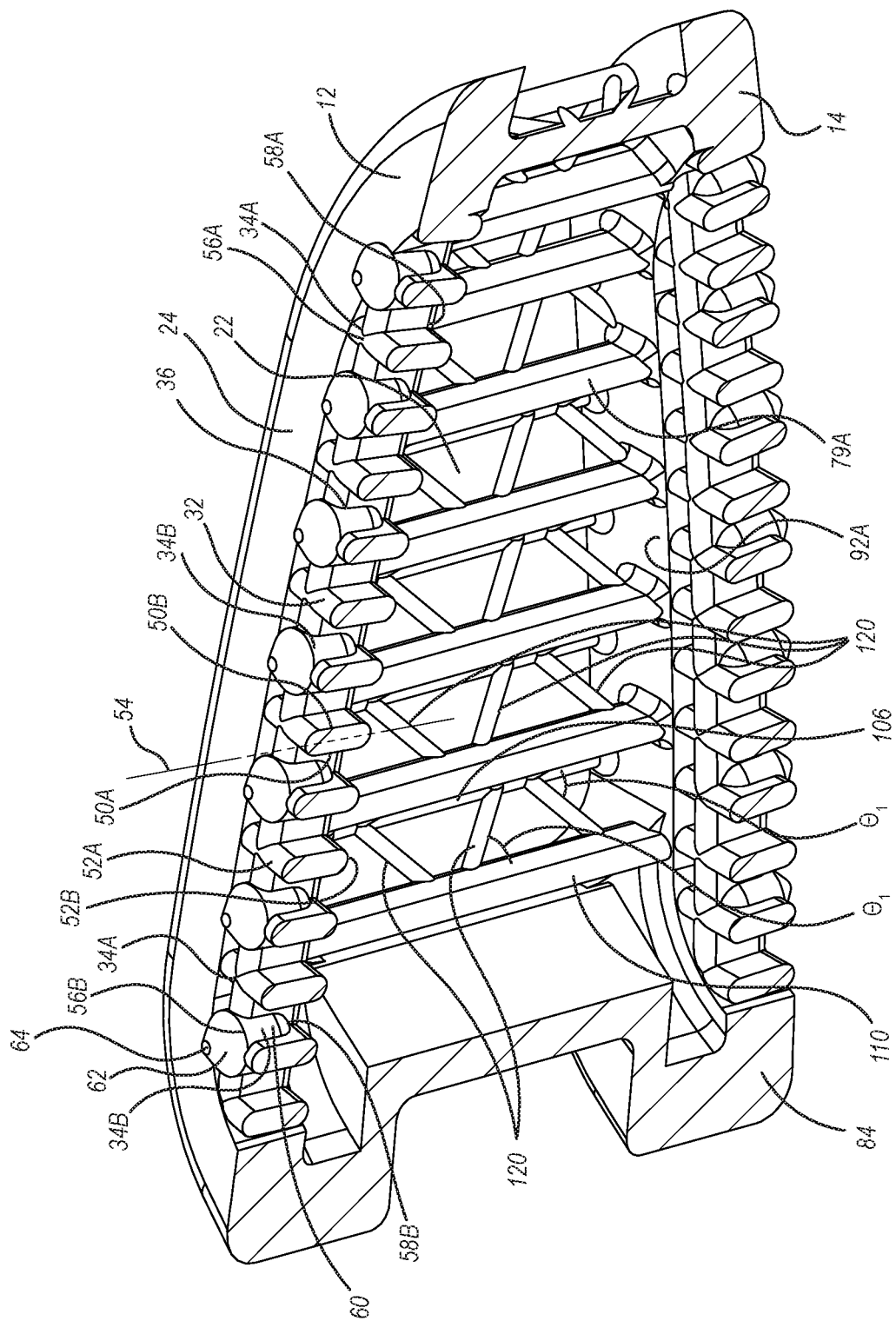
FIG. 5 is a cross sectional side view of the fusion implant shown in FIG. 1.

As depicted in FIG. 5, rods 32 can have an elongated transverse cross section with opposing parallel sides 50A and 50B and opposing rounded ends 52A and 52B. The distance between sides 50A and 50B is narrower than the distance between ends 52A and 52B and rods 32 are orientated so that a longitudinal axis 54 extending through ends 52A and 52B extends into cavity 22. This configuration and orientation of rods 32 achieves a number of benefits. For example, fusion implant 10 is primarily subject to compression loads applied between top wall 12 and bottom wall 14. As a result of their configuration and orientation, rods 32 maximize their resistance to bending and failure under the compressive load while also maximizing the size of openings 36 between rods 32, thereby enhancing bone growth through implant 12. In alternative embodiments, however, rods 32 can have a transverse cross section that is circular, rectangular, elliptical, polygonal or have other configurations.

Continuing with FIG. 5, junction nodes 34 formed at the intersection of rods 32 can have a variety of different configuration. For example, junction nodes 34 can comprise junction nodes 34A and 34B. Junction nodes 34A simply comprise an intersection of rods 32 without a change of shape in rods 32. Junction nodes 34A include a top surface 56A and an opposing bottom surface 58A. Bottom surface 58A can terminate at and be openly exposed within cavity 22, i.e., there is no structure attached to or extending from bottom surface 58A. In contrast, junction nodes 34B can comprise an enlarged junction body 60 into which rods 32 intersect and which have a different configuration than rods 32. For example, each junction body 60 can have a transverse cross section with a maximum diameter that is larger than the thickness between sides 50A and 50B of rods 32. In the depicted embodiment, junction body 60 can have a circular transverse cross section. In other embodiments, the transverse cross section of junction body 60 can be elliptical, polygonal or have other shapes. Junction node 34B also has a top surface 56B located on top of junction body 60 and an opposing bottom surface 58B that is again freely exposed within cavity 22.

Each junction body 60 is configured to support a tooth. Specifically, upwardly projecting from top surface 56B of junction body 60 is a tooth 62. Tooth 62 tapers inwardly from top surface 56B to a point 64. In the depicted embodiment, tooth 62 has a conical configuration. In other embodiments, tooth 62 could have pyramidal configuration or other inwardly tapered configuration where the base of tooth 62 is complementary to the top surface 56B of junction body 60. Teeth 62 are used for engaging the adjacent vertebra during use. Junction body 60 is formed to provide structural support teeth 62, i.e., enabling teeth 62 to have a larger base, and also provides increased structural support for the intersection of rods 32 that can have increased load resulting from pressure against teeth 62. In contrast, junction nodes 34A, where no teeth 62 are positioned, are commonly formed without junction body 60 so as to maximize the size of openings 36 and thus enhance bone growth through implant 10.

Returning to FIG. 1, the network of interconnected rods 32 can be disposed in a uniform pattern and can be disposed in a common plane. Furthermore, depending on the configuration and intended use, it is also noted that portions of top outer perimeter rail 24 and top inner perimeter rail 26 can directly connect together, as shown in FIG. 1, so that no top grating 30 extends therebetween.

Turning to FIG. 2, bottom wall 14 includes a bottom outer perimeter rail 84 and a bottom inner perimeter rail 86. Bottom inner perimeter rail 86 is disposed radially inward from bottom outer perimeter rail 84 and bounds a bottom access 88 that communicates with cavity 22. With reference to FIG. 12, bottom outer perimeter rail 84 and bottom inner perimeter rail 86 can have the same configuration as top outer perimeter rail 24 and top inner perimeter rail 26, respectively. For example, although not required, bottom outer perimeter rail 84 and bottom inner perimeter rail 86 are again depicted as having a substantially rectangular transverse cross section. More specifically, bottom outer perimeter rail 84 has a top surface 91A and an opposing bottom surface 92A that extend between an interior surface 93A and an opposing exterior surface 94A. Interior surface 93A faces toward bottom inner perimeter rail 86. Bottom inner perimeter rail 86 also has a top surface 115A and an opposing bottom surface 116A that extend between an interior surface 117A and an opposing exterior surface 118A. Interior surface 117A bounds bottom access 88. Bottom outer perimeter rail 84 and bottom inner perimeter rail 86 both typically form a continuous loop and form a solid structural member.

Bottom wall 14 also includes a bottom grating 90 that extends from the bottom outer perimeter rail 84 to bottom inner perimeter rail 86. As with top grating 30, bottom grating 90 also comprises a network of interconnecting rods 32 that join together at junction nodes 34 and that bound a plurality of openings 36 that communicate with cavity 22, as depicted in FIG. 2. The above discussion of rods 32, junction nodes 34 and openings 36 made in association with top grating 30 is also applicable to bottom grating 90. By way of example and not by limitation, the above discussion of configurations, orientations, alternatives, uses and benefits discussed above with regard to rods 32, junction nodes 34 and openings 36 of top grating 30 are also applicable to rods 32, junction nodes 34 and openings 36 of bottom grating 90.

Returning to FIG. 1, front wall 40 is in the form of a plate having exterior front face 74 and interior front face 75 that extend vertically between top outer perimeter rail 24 and bottom outer perimeter rail 84. Front wall 40 also extends laterally between side walls 44 and 46. Interior front face 75 partially bounds cavity 22 while exterior front face 74 is openly exposed. Screw holes 96A, 96B and 96C extend through front wall 40 between exterior front face 74 and interior front face 75 so as to communicate with cavity 22. Screw holes 96A and 96C are angled upward toward top wall 12 while screw hole 96B is angle downward to bottom wall 14. Screw holes 96A and 96C are configured to receive bone screws and are angled as set forth above so that during use, when implant 11 is disposed between vertebra, bone screws passed through screw holes 96A, 96B and 96C, through top access 28 or bottom access 88, and thread into the adjacent vertebra for securely holding fusion implant 10 in position.

In alternative embodiments, alternative numbers and orientations of screw holes 96 can be used. For example, fusion implant 10 can include one, two, or four of more screw holes 96. In other embodiments, as discussed below in greater detail, fusion implants of the present invention can be made without any screw holes. In those embodiments, the fusion implants can initially be held by friction between the vertebra. The number and whether or not a fusion implant has screw holes 96 is in part dependent upon where and how the fusion implant will be used. Notches 100A and 100B are recessed into exterior front face 74 at the opposing lateral ends thereof and can be engaged by an insertion tool during placement of fusion implant 10. In alternative embodiments, notches 100 can have different configurations or positions or can be eliminated.

Figure 6:
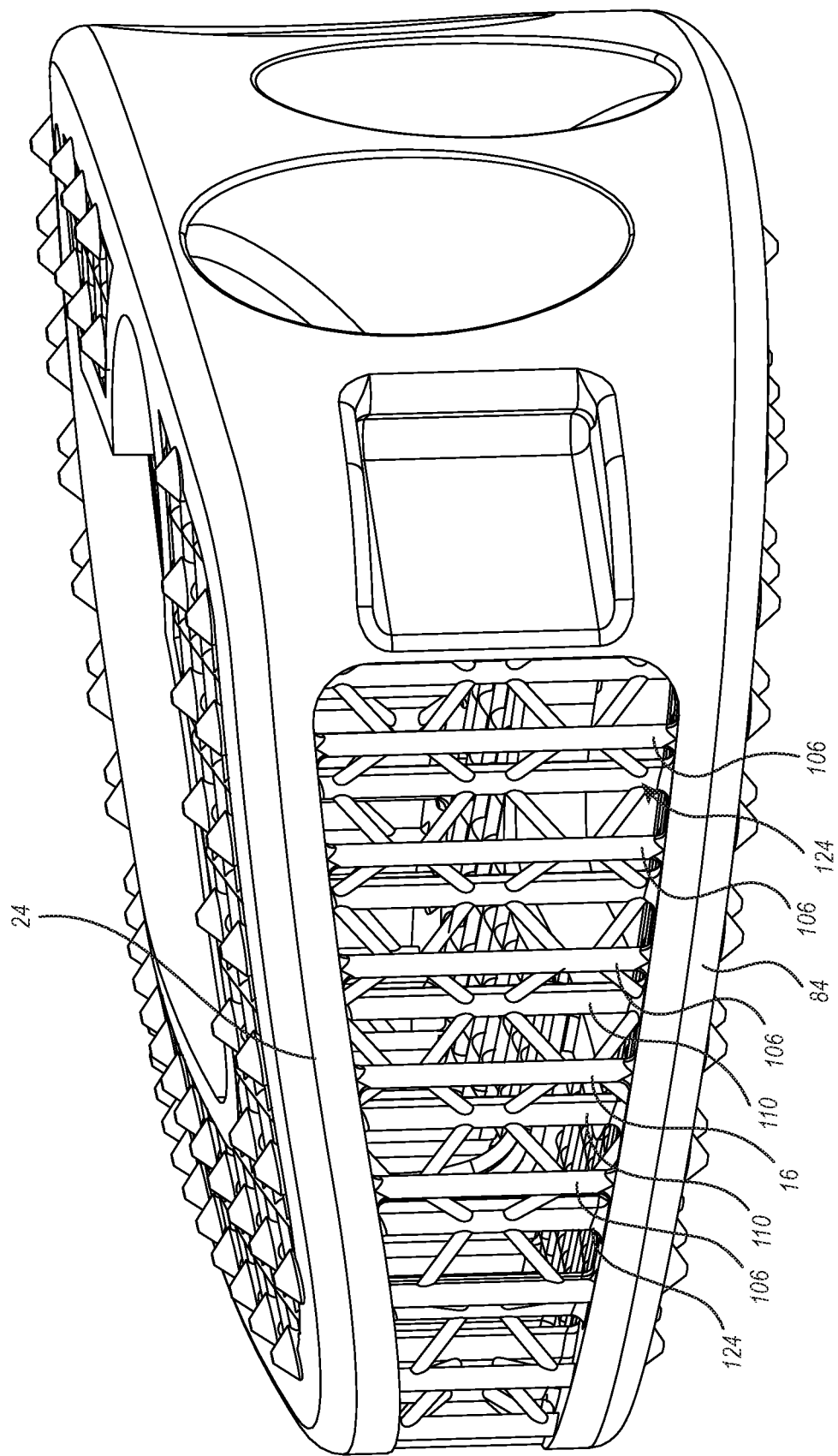
FIG. 6 is a left side perspective view of the implant shown in FIG. 1.
Figure 7:
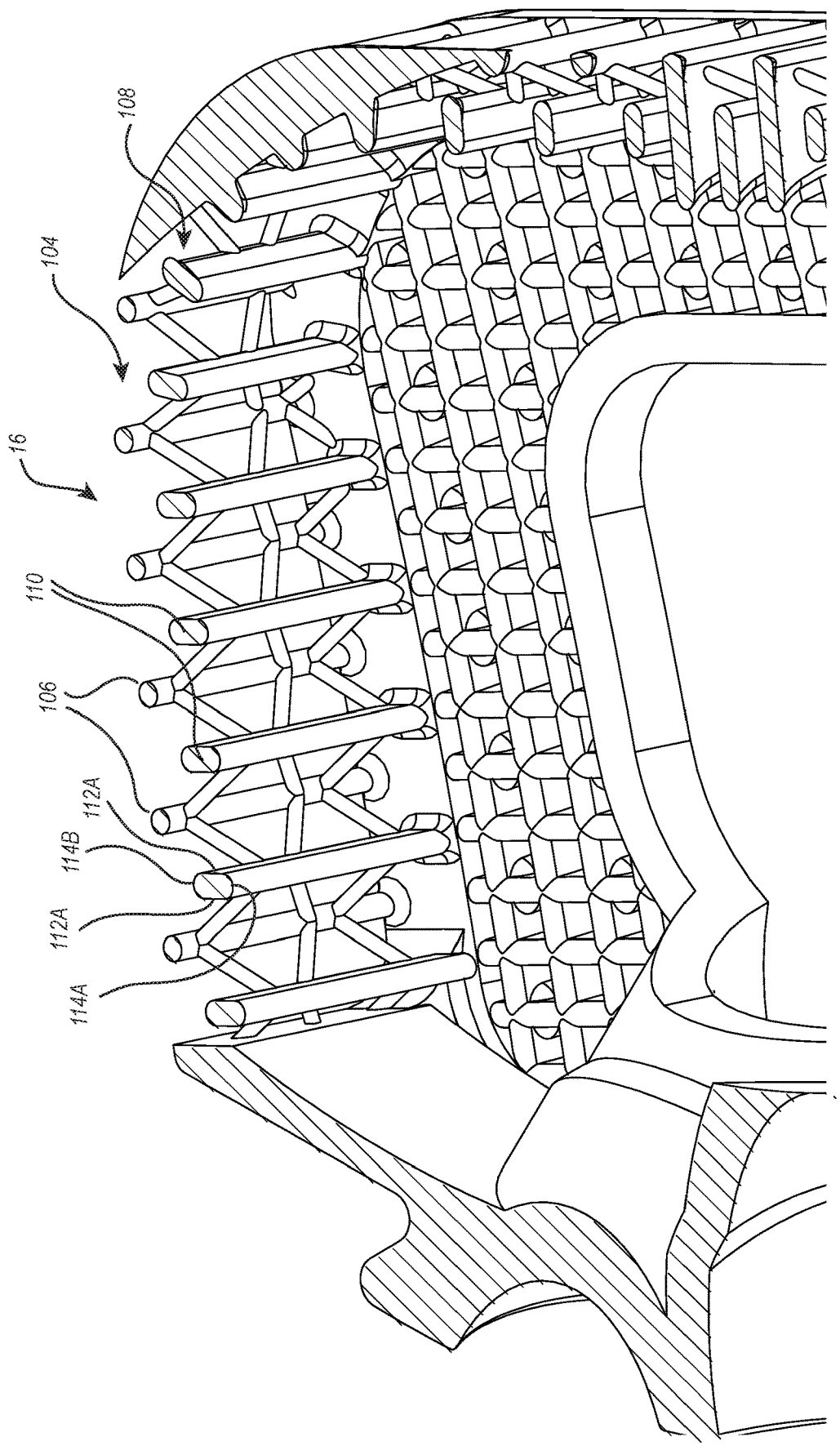
FIG. 7 is a cross sectional top perspective view of the fusion implant shown in FIG. 1.

In contrast to front wall 40 that is in the form of a plate, back wall 42 and side walls 44 and 46 are comprised of spaced apart struts. Specifically, as depicted in FIGS. 5 and 6, side wall 44 comprises a row 104 of a plurality of spaced apart outer struts 106 that extend between top wall 12 and bottom wall 14 and, more specifically, extend between bottom surface 92 (FIG. 12) of top outer perimeter rail 24 and bottom surface 92A of bottom outer perimeter rail 84. Side wall 44 further comprises a row 108 of a plurality of spaced apart inner struts 110 that extend between top wall 12 and bottom wall 14, more specifically, extend between bottom surface 92 (FIG. 12) of top outer perimeter rail 24 and bottom surface 92A of bottom outer perimeter rail 84. Row 108 of inner struts 110 is set back a distance from row 104 of outer struts 106 toward cavity 22.

In the depicted embodiment, outer struts 106 are linear and are disposed in parallel alignment. Further, at least a portion of row 104 is linear. For example, at least 3, 4, 5, 6, 7 or more of outer struts 106 can be aligned in a linear row. Row 104 can also be curved, which curve can change at different locations, and can be a combination where a portion of row 104 is linear and a portion of row 104 are curved. In the depicted embodiment, each outer strut 106 has a transverse cross section that is circular. However, in other embodiments, the transverse cross section of each outer strut 106 can be elliptical, rectangular, polygonal, irregular or have other configurations. For example, as with rods 32, and discussed below with regard to inner struts 110, outer strut 106 can have an elongated transverse cross section having flat opposing parallel sides and opposing rounded ends. Other configurations can also be used. The number of outer struts 106 in row 104 for a given wall is dependent in part on the length of the wall. However, it is common to have at least or less than 3, 5, 6, 7, 9, 11, 13, 15, 20 or 25 outer struts 106 in row 104 for a given wall. The number of outer struts can also be in a range between any two of the foregoing.

Inner struts 110 can have substantially the same configuration and layout as outer struts 106 as discussed above. More specifically, inner struts 110 are depicted as being linear and disposed in parallel alignment. Further, at least a portion of row 108 is linear. For example, at least 3, 4, 5, 6, 7 or more of inner struts 110 can be aligned in a linear row. Row 108 can also be curved, which curve can change at different locations, and can be a combination where a portion of row 108 is linear and a portion of row 108 is curved. In the depicted embodiment, each inner strut 110 has transverse cross section that is elongated having opposing flat parallel sides 112A and 112B and opposing rounded ends 114A and 114B. However, in other embodiments, the transverse cross section of each inner strut 110 can be elliptical, circular, polygonal or other irregular configurations. Other configurations can also be used. The number of inner struts 110 in row 108 for a given wall is dependent in part on the length of the wall. However, it is common to have at least or less than 3, 5, 6, 7, 9, 11, 13, 15, 20 or 25 inner struts 110 in row 108 for a given wall. The number of inner struts 110 can also be in a range between any two of the foregoing.

Figure 8:
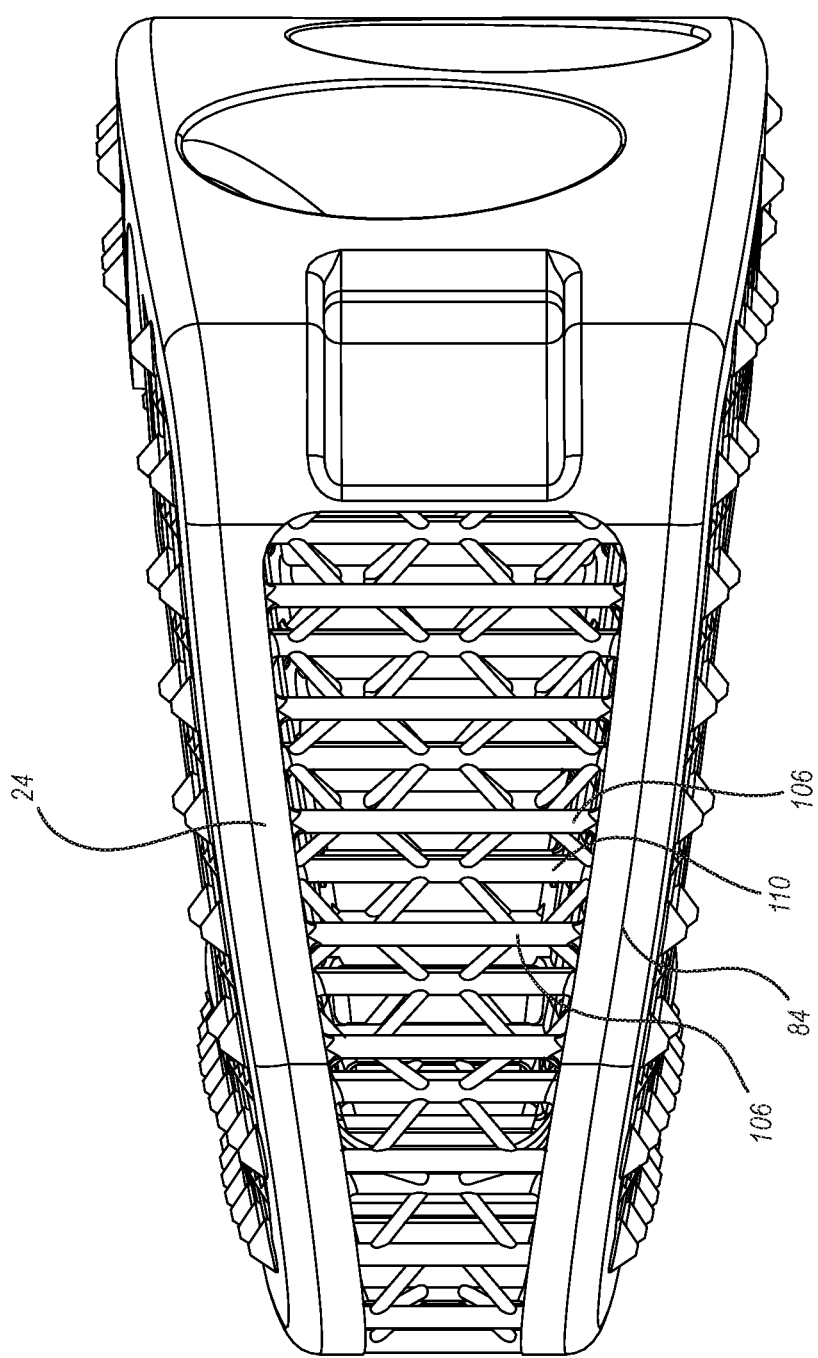
FIG. 8 is an elevated left side view of the implant shown in FIG. 1.

In the depicted embodiment, outer struts 106 are disposed parallel to inner struts 110. Furthermore, inner struts 110 are staggered so that each inner strut 110 is disposed between an adjacent pair of outer struts 110. More specifically, struts 106 and 110 are positioned so that when side wall 44 is viewed in a front elevational view, as depicted in FIG. 8, each inner strut 110 is disposed between, and preferably centrally disposed between, an adjacent pair of outer struts 110. One of the functional benefits of this layout will be discussed below in more detail.

Figure 9:
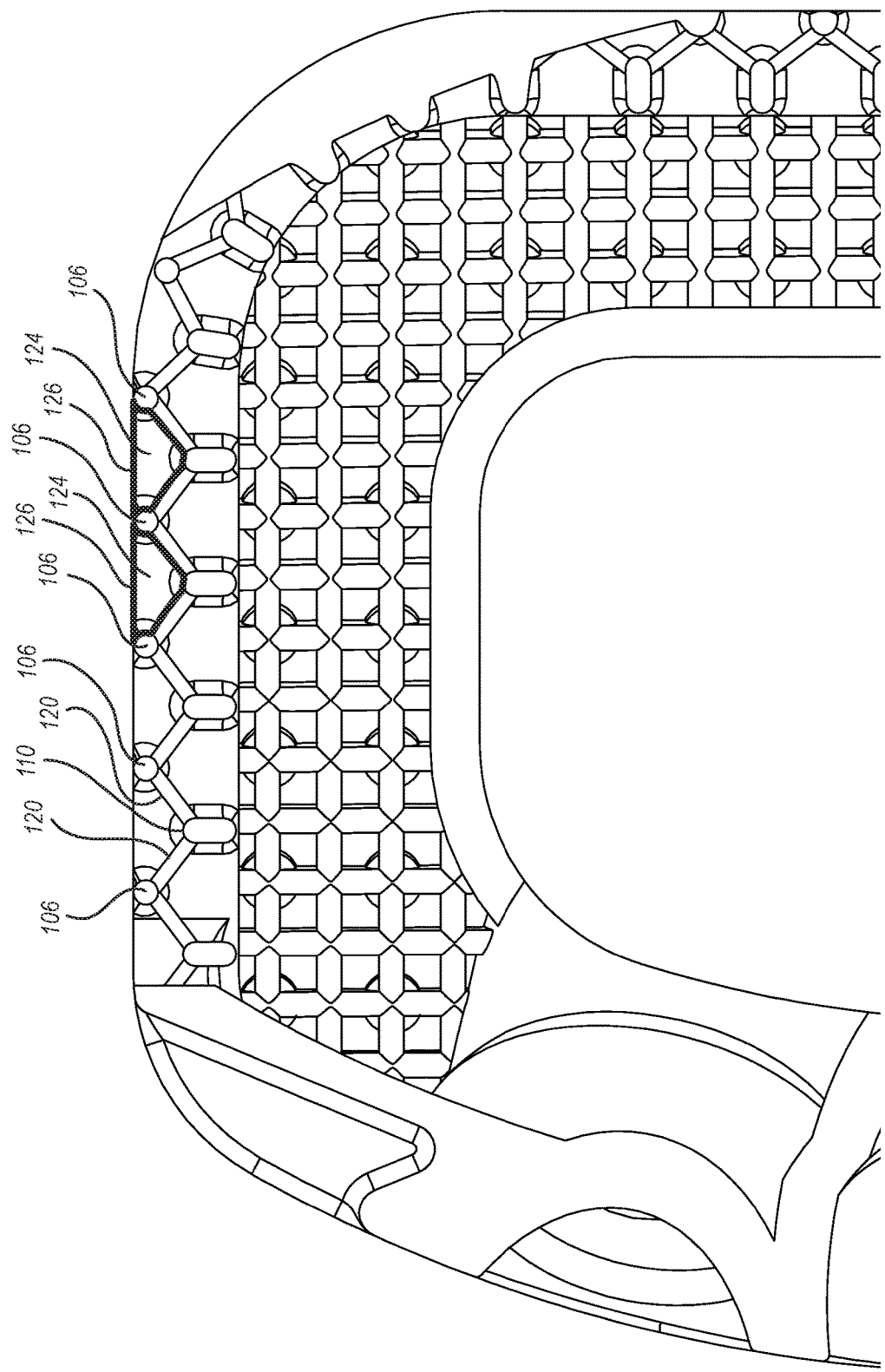
FIG. 9 is a cross sectional top plan view of the implant shown in FIG. 1.

Returning again to FIGS. 5 and 6, support members 120 extend between outer struts 106 and inner struts 110. Support members 120 assist in providing lateral support for struts 106 and 110 and thus help prevent buckling when loaded. More specifically, for a given inner strut 110, separate support members 120 outwardly extend from the given inner strut 110 to each of the adjacent pair of outer struts 106. Thus, support members 120 connect each inner strut 110 to two adjacent outer struts 106. Likewise, support members 120 connect each outer strut 106 to two adjacent inner struts 110. Thus, when viewed in the top plan view shown in FIG. 9, inner strut 110, outer struts 106, and support members 120 produce a zigzag pattern.

Furthermore, with reference to FIG. 5, for each adjacent pair of an inner strut 110 and an outer strut 106, a plurality of support members 120 can extend therebetween. In the depicted embodiment, support members 120 project at angles between the inner strut 110 and outer strut 106 so that again support member 120 can form a zigzag pattern extending between the pair of the inner strut 110 and outer strut 106. For example, support members 120 extends so that an inside angle θ1 is formed between support member 120 and inner strut 110 or outer strut 106 that is in a range between 20° and 70° and more commonly between 30° and 60° or 40° and 50°. However, in other embodiments, support members 120 can extend perpendicular from inner strut 110 and outer strut 106 or at an angle θ1 that is between 80° and 110°. It is noted that some support member 120 extend between inner struts 110 and outer struts 106 without contacting top wall 12 or bottom wall 14, i.e., without contacting top outer perimeter rail 24 or bottom outer perimeter rail 84. Furthermore, although not required, in the depicted embodiment, no support members 120 or other structures extend between adjacent pairs of outer struts 106 or adjacent pairs of inner struts 110.

Support members 120 can have a transverse cross section that is the same configuration as the transverse cross section of inner strut 110 or outer strut 106, as previously discussed. However, support members 120 will typically have a transverse cross sectional area that is small than the transverse cross sectional area of inner strut 110 and outer strut 106 because support members 120 are subject to a lower load than inner struts 110 and outer struts 106 during use.

The foregoing discussion of inner struts 110, outer struts 106, and support members 120 and the alternatives discussed thereto are also applicable to back wall 42 and other side wall 46 and like elements are identified by like reference characters. As depicted in the drawings, however, the lengths of inner struts 110, outer struts 106, and support members 120 can vary based on location. For example, where fusion implant 10 is wedged shaped, as depicted, the lengths of inner struts 110 and outer struts 106 are, on average, shorter on back wall 42 than on side wall 44 and 46.

It is appreciated that fusion implant 10 has a number of unique configurations and achieves a number of unique benefits and advantages. For example, one of the objectives of fusion implant 10 is to enhance rapid bone growth into, through and around fusion implant 10 so that the time period of complete fusion between adjacent vertebrae is decreased, thereby decreasing patient recovery time. In the depicted configuration of fusion implant 10, an open column 124 (FIG. 6) is formed between each adjacent pair of outer struts 106 and comprises the openly exposed area that extends between top outer perimeter rail 24 and bottom outer perimeter rail 84 and is freely exposed to the area outside of fusion implant 10. As marked by line 126 in FIG. 9, open column 124 has a triangular transverse cross section extending between top outer perimeter rail 24 and bottom outer perimeter rail 84 with an adjacent pair of outer struts 106 bounding two corners and the centrally located inner strut 110 bounding the third corner. Support members 120 extending between the centrally located inner strut 110 to each of the adjacent outer struts 106 partially bound two of the walls of open column 124 while the third wall is openly exposed to the outside environment. Open columns 124 are formed along each of walls 42, 44, and 46. The benefit of open columns 124 is that bone can easily grow into each open column 124 from outside of fusion implant 10 because the bone is not obstructed by any elements of implant 10. In turn, as bone grows from the adjacent vertebra into open columns 124, the bone is captured between top outer perimeter rail 24 and bottom outer perimeter rail 84 which functions to lock implant 10 to the adjacent vertebra early in the bone growth process, thereby helping to prevent unwanted movement of fusion implant 10 and thus enhancing rapid final fusion between fusion implant 10 and the adjacent vertebra.

Other features of fusion implant 10 are also designed to optimize rapid bone growth into fusion implant 10. For example, outer struts 106 are typically, although not required, formed smaller than inner struts 110 so as to maximize the openings to columns 124, thereby further enhancing bone growth into implant 10. Likewise, outer struts 106, inner struts 110, and support members 124 are uniquely designed to maximize the open space therebetween so as to enhance the speed and uniformity at which bone can laterally grow around struts 106 and 110 and into cavity 22. For example, by having two spaced apart rows of struts 106 and 110, as opposed to a single row of enlarged struts, the inventive design is able to improve the uniform growth of bone into fusion implant 10 and also optimize the volume of bone growth into fusion implant 10, thereby again enhancing early stabilization of fusion implant 10 and improving the final overall strength of the fused vertebra.

In addition, fusion implant 10 is uniquely configured so that outer struts 106, inner struts 110 and support members 124 are the only supports that extend between top wall 12 and bottom wall 14 and are disposed between top outer perimeter rail 24 and bottom outer perimeter rail 84. That is, there are no structural members disposed radially inward of top outer perimeter rail 24 and bottom outer perimeter rail 84 that extend between top wall 12 and bottom wall 14. As a result, the size of cavity 22 is maximized so as to maximize the amount of bone growth material that can be received therein. Furthermore, the bone growth material can be easily and efficiently packed into cavity 22 without interference of structural members within cavity 22.

Furthermore, top grating 30 and bottom grating 90 are designed to both capture bone growth material within cavity 22 and maximize the size, quantity and uniform dispersion of openings 36 extending therethough so as to maximize and uniformly disperse vertical bone growth through implant 10. The outer perimeter rails 24, 84 and inner perimeter rails 26, 86 are also designed to stabilize and strengthen top grating 30 and bottom grating 90 so as to help eliminate the need for other structural supports extending between top wall 12 and bottom wall 14 and to permit maximizing the size of openings 36 to improve vertical bone growth through fusion implant 10.

In view of the foregoing, each of the different elements of fusion implant 10 have been uniquely configured to either independently or in combination with other parts improve the functionality and performance of fusion implant 10. It is appreciated, however, that in other alternative embodiments of the present invention that not all of the disclosed novel features need to be incorporated into a single fusion implant but that different novel features can be independently used or used in different combination in different implants and still achieve beneficial results and solve existing problems in the art.

Figure 10:
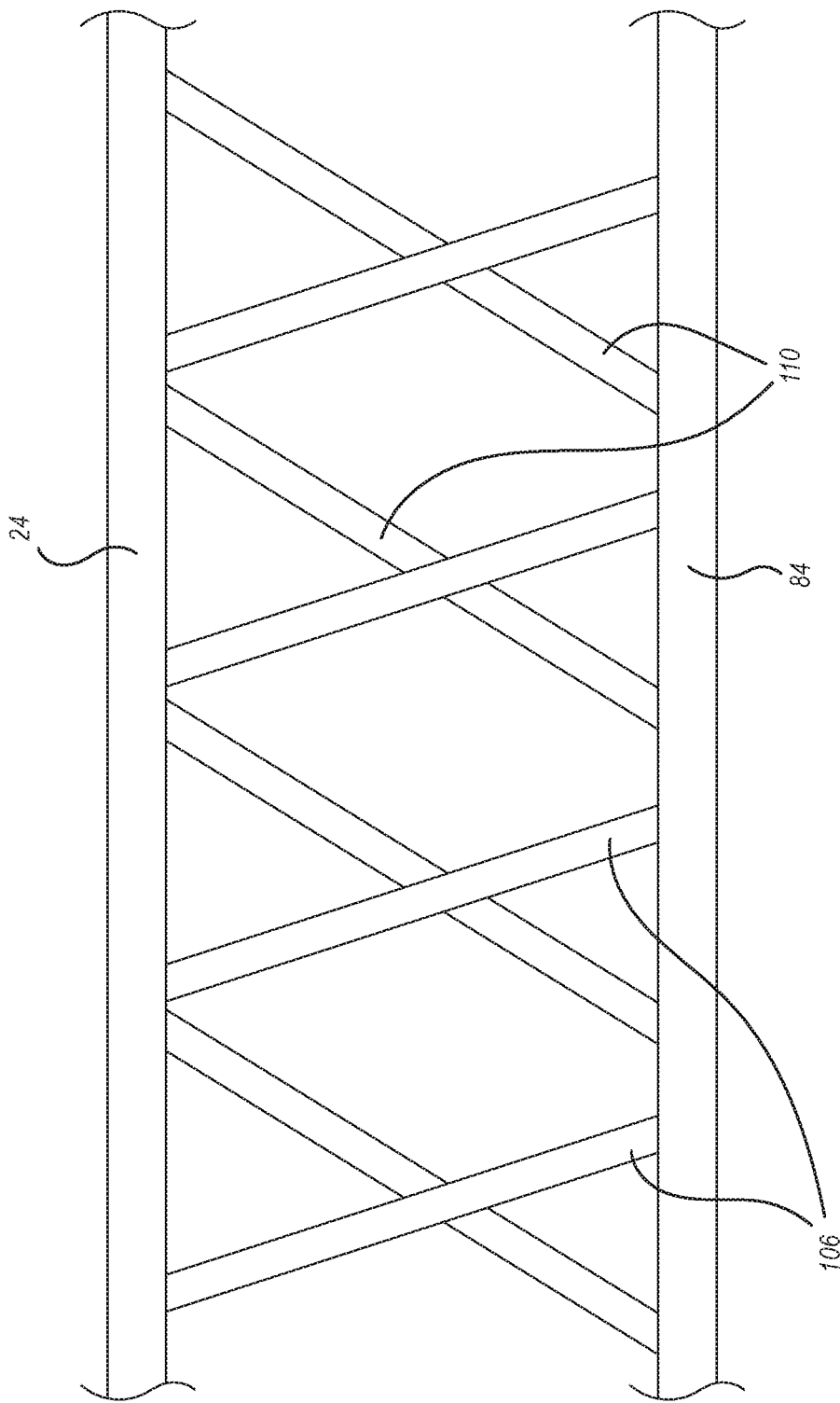
FIG. 10 is an elevated front view of an alternative embodiment of inner struts and outer struts extending between the top outer perimeter rail and the bottom outer perimeter rail of the fusion implant shown in FIG. 1.

It is also appreciated that the features of the present invention can be modified in a variety of different ways. By way of example and not by limitation, FIG. 10 shows that not only can outer struts 106 and inner struts 110 be angled relative to top outer perimeter rail 24 and bottom outer perimeter rail 84 over a wide range of angles but also that outer struts 106 need not be parallel to inner struts 110. That is, although all of outer struts 106 may be disposed in parallel alignment and all of inner struts 110 may be disposed in parallel alignment, outer struts 106 can be disposed at a different angle than inner struts 110 relative to top outer perimeter rail 24 and bottom outer perimeter rail 84. Furthermore, as depicted in FIG. 10, outer struts 106 can be sloped in an opposite direction to inner struts 110.

Figure 11:
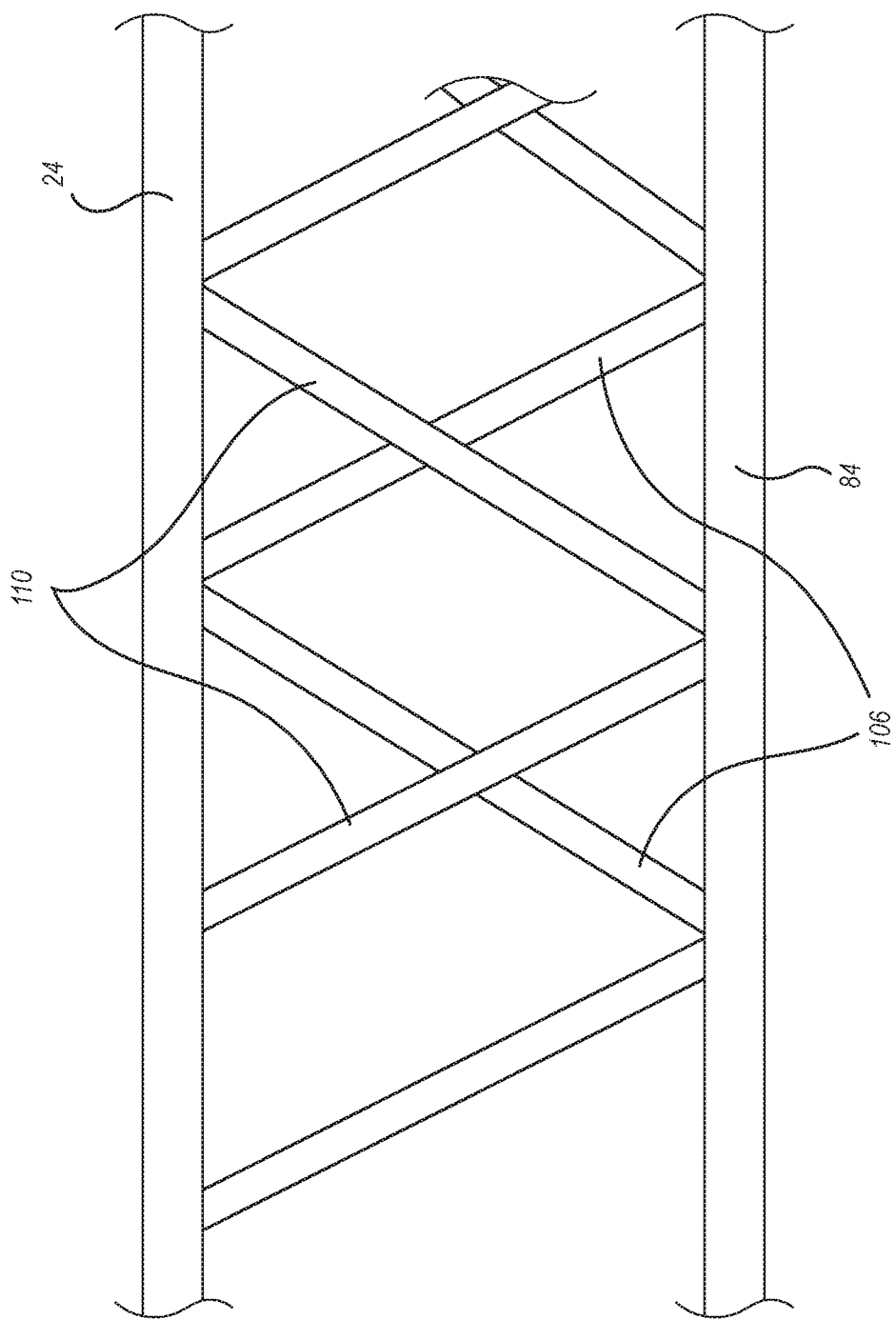
FIG. 11 is an elevated front view of another alternative embodiment of inner struts and outer struts extending between the top outer perimeter rail and the bottom outer perimeter rail of the fusion implant shown in FIG. 1.

In another alternative as depicted in FIG. 11, outer struts 106 need not be disposed in parallel alignment relative to each other and inner struts 110 need not be disposed in parallel alignment relative to each other. For example, alternating outer struts 106 can be sloped in opposite directions and alternating inner struts 110 can be sloped an opposite directions so that both outer struts 106 and inner struts 110 are disposed a zigzag pattern. In all of the above alternatives for outer struts 106 and inner struts 110, support members 120 can be placed at different angles and at different locations between outer struts 106 and inner struts 110. Alternatively, depending on the size and location of outer struts 106 and inner struts 110, support members 120 can be eliminated. It is appreciated that having outer struts 106 and inner struts 110 in the configurations as depicted in FIGS. 10 and 11 achieves many of the same benefits as previously discussed above with regard to fusion implant 10. For example, having the spaced apart rows of outer struts 106 and inner struts 110 still provides uniform and large openings for lateral bone growth in fusion implant 10 and still maximizes the size of cavity 22 without requiring other support structures extending between top wall 12 and bottom wall 14.

Figure 13:
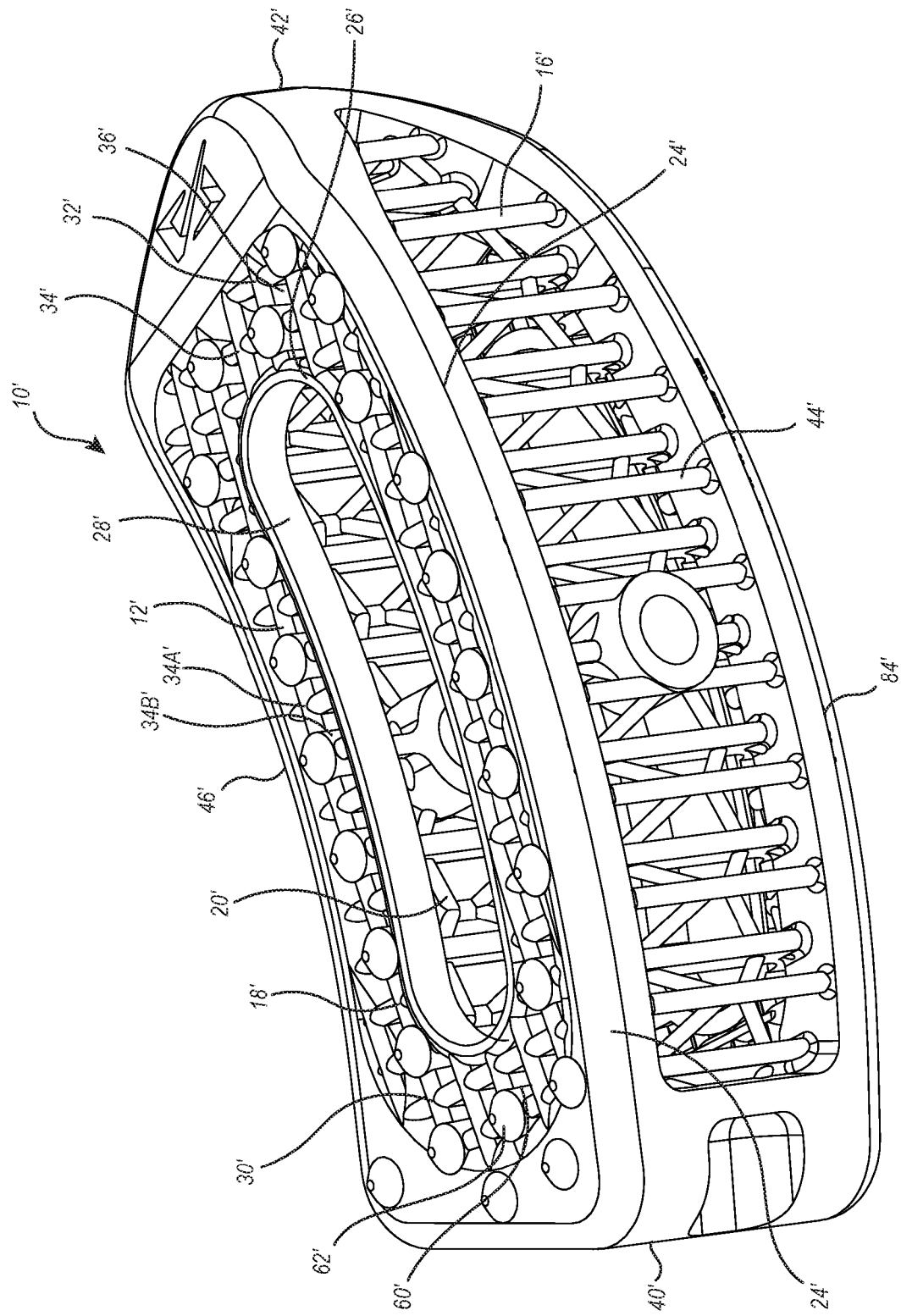
FIG. 13 is a top, side perspective view of an alternative embodiment of the fusion implant shown in FIG. 1.
Figure 14:
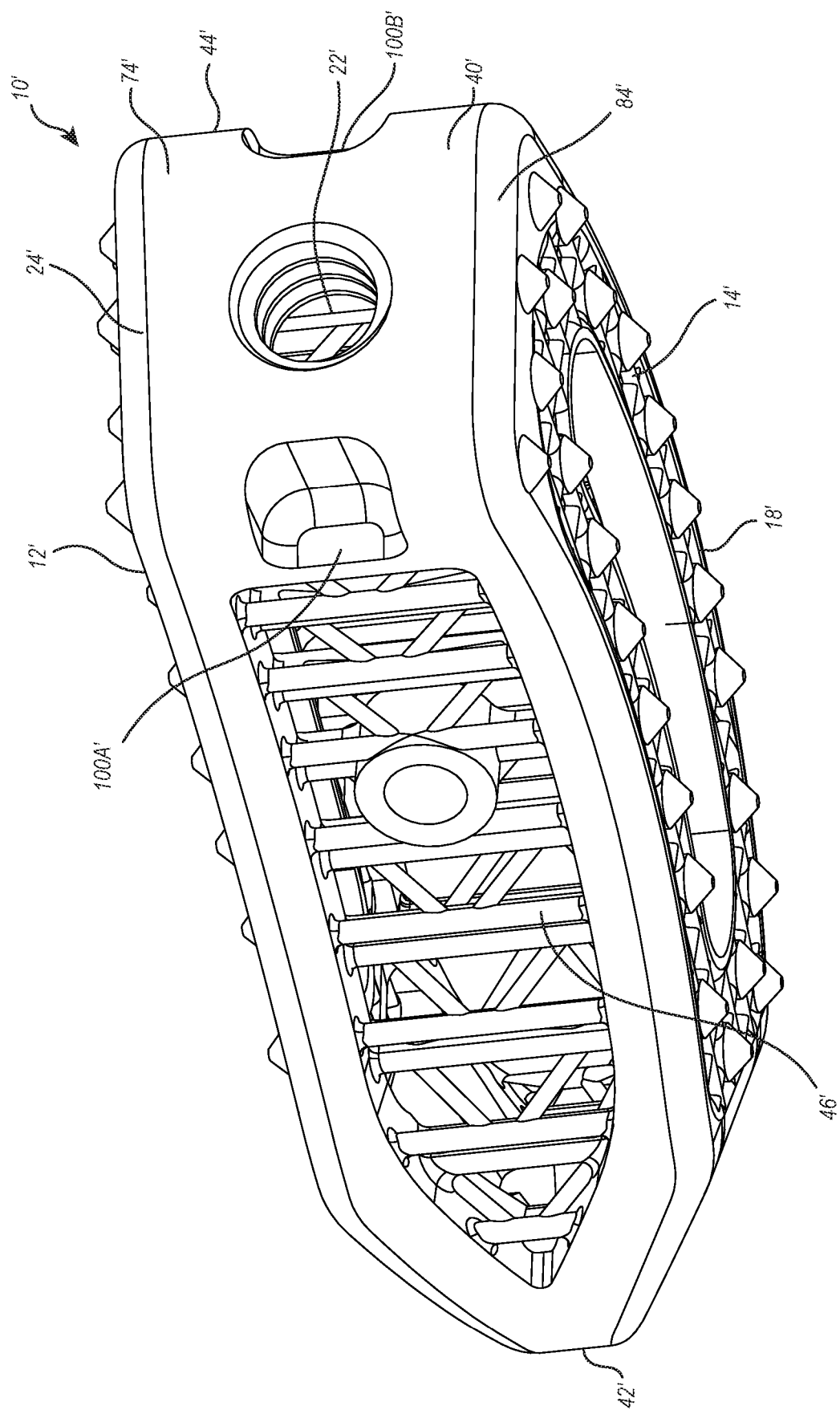
FIG. 14 is a bottom, back perspective view of the fusion implant shown in FIG. 13.
Figure 15:
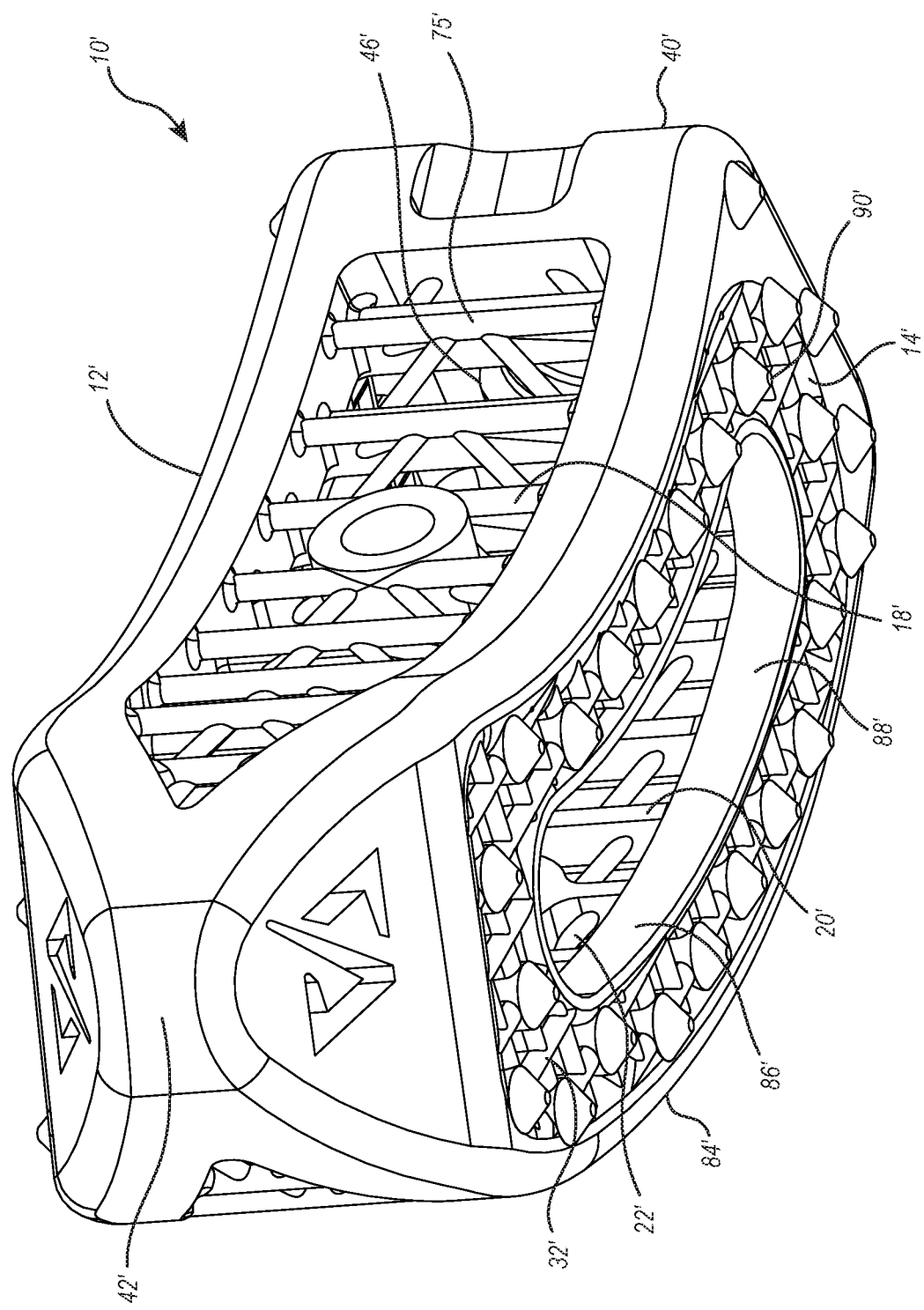
FIG. 15 is front, bottom perspective view of the fusion implant shown in FIG. 13.

As previously discussed, the configuration of implant 10 as depicted in FIGS. 1 and 2, is only one design for the current technology. In addition to the above discussed alternatives, however, the design can also change depending on the intended use of the fusion implant. For example, depicted in FIGS. 13-15 are views of an interbody spinal fusion implant 10' incorporating features of the present invention that is designed for use in a transforaminal lumbar interbody fusion (TLIF) surgery. Like elements between fusion implants 10 and 10' will be identified by like reference characters except that a "'" will be added to each of the reference numbers associated with fusion implant 10'. For all like elements, the prior discussion for that element, including configurations, layouts, orientations, elements, alternatives, uses, benefits, advantages and the like, are also applicable for the corresponding element of fusion implant 10', unless expressly stated or inherently understood otherwise. For example, junction nodes 34' include the same configurations, layouts, orientations, elements, alternatives, uses, benefits, and advantages as junction nodes 34 previously discussed.

In general, as depicted in FIGS. 13-15, fusion implant 10' comprises top wall 12', spaced apart bottom wall 14' and encircling sidewall 16' extending therebetween. Sidewall 16' includes front wall 40', back wall 42', and opposing side walls 44' and 46' that extend between walls 40' and 42'. Fusion implant 10' has exterior surface 18' and interior surface 20'. Interior surface 20' at least partially bounds cavity 22' in which a bone growth material, as discussed above, can be packed during use of fusion implant 10'.

Continuing with FIG. 12, top wall 12' includes top outer perimeter rail 24' and top inner perimeter rail 26'. Top inner perimeter rail 26' is disposed radially inward from top outer perimeter rail 24' and bounds top access 28' that communicates with cavity 22'. Top outer perimeter rail 24' and top inner perimeter rail 26' both typically form a continuous loop and form a solid structural member. Top wall 12' also includes top grating 30' that extends from top outer perimeter rail 24' to top inner perimeter rail 26'.

Top grating 30' comprises the network of interconnecting rods 32' that join together at junction nodes 34' and that bound a plurality of openings 36' that communicate with cavity 22. Junction nodes 34' include junction nodes 34A' and 34B' and include tooth 62' projecting from junction body 60'.

Turning to FIG. 15, bottom wall 14' includes bottom outer perimeter rail 84' and a bottom inner perimeter rail 86'. Bottom inner perimeter rail 86' is disposed radially inward from bottom outer perimeter rail 84' and bounds bottom access 88' that communicates with cavity 22'. Bottom outer perimeter rail 84' and bottom inner perimeter rail 86' both typically form a continuous loop and form a solid structural member. Bottom wall 14' also includes a bottom grating 90' that extends from bottom outer perimeter rail 84' to bottom inner perimeter rail 86'. As with top grating 30', bottom grating 90' also comprises the network of interconnecting rods 32' that join together at junction nodes 34' and that bound the plurality of openings 36' that communicate with cavity 22'.

Returning to FIG. 14, front wall 40' is in the form of a plate having exterior front face 74' and interior front face 75' (FIG. 15) that extend vertically between top outer perimeter rail 24' and bottom outer perimeter rail 84'. Front wall 40' also extends laterally between side walls 44' and 46'. Interior front face 75' partially bounds cavity 22' while exterior front face 74' is openly exposed. Front wall 40' does not include screw holes 96 but rather includes a threaded mounting hole 130 extend through front wall 40' between exterior front face 74' and interior front face 75' so as to communicate with cavity 22'. Mounting hole 130 is configured to threadedly receive an insertion tool that is used for placing fusion implant 10' between vertebra. Once fusion implant 10' is positioned, the insertion tool is removed. Fusion implant is then initially held in place by friction between the vertebrae. Again, as needed, one or more screw holes 96 can be formed through front wall 40' and also through top wall 12' and/or bottom wall 14'. Notches 100A' and 100B' are recessed into exterior front face 74' at the opposing lateral ends thereof and can be used for engaging with the insertion tool during the placement of implant 10'.

Figure 16:
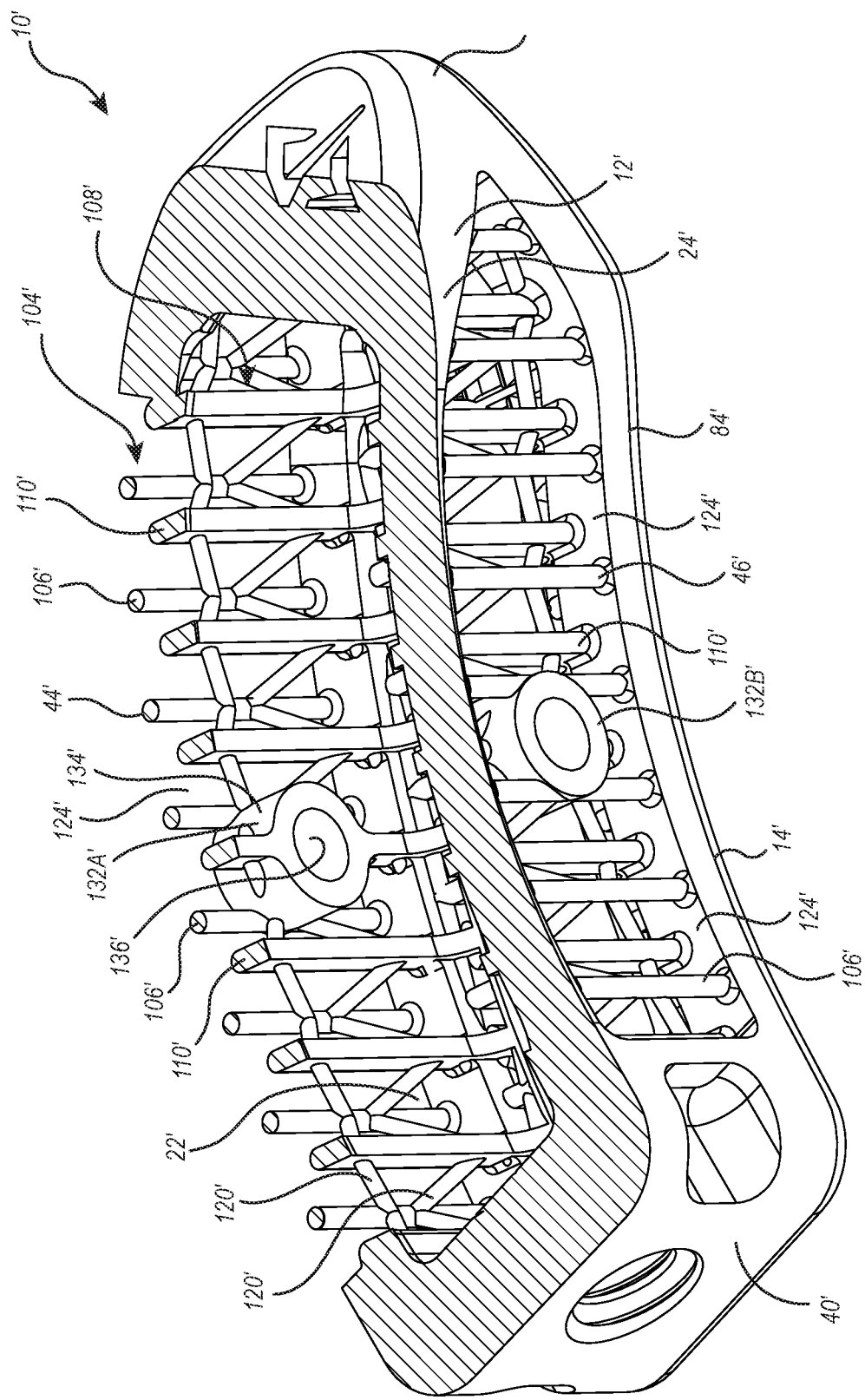
FIG. 16 is a cross sectional, top perspective view of the fusion implant shown in FIG. 13.

In contrast to front wall 40' which is in the form of a plate, side walls 44' and 46' are comprised of spaced apart struts. Specifically, as depicted in FIG. 16, side wall 44' comprises row 104' of the plurality of spaced apart outer struts 106' that extend between top wall 12' and bottom wall 14' and, more specifically, extend between top outer perimeter rail 24' and bottom outer perimeter rail 84'. Side wall 44' further comprises row 108' of the plurality of spaced apart inner struts 110' extending between top wall 12' and bottom wall 14', more specifically, extending between top outer perimeter rail 24' and bottom outer perimeter rail 84'. Row 108' of inner struts 110' are set back a distance from row 104' of outer struts 106' toward cavity 22'.

In the depicted embodiment, as with the prior embodiment, outer struts 106' are disposed in parallel alignment with each other and inner struts 110' are disposed in parallel alignment with each other. In addition, outer struts 106' are disposed in parallel alignment with inner struts 110'. Inner struts 110' are also staggered so that each inner strut 110' is disposed between an adjacent pair of outer struts 106'. More specifically, struts 106' and 110' are positioned so that when side wall 44 is viewed in a front elevational view, each inner strut 110' is disposed between, and preferably centrally disposed between, an adjacent pair of outer struts 110'. Again, as previously discussed, outer struts 106' and inner struts 110' can also be disposed at other orientations.

Support members 120' extend between outer struts 106' and inner struts 110'. More specifically, for a given inner strut 110', separate support members 120' outwardly extend from the inner strut 110' to each of the adjacent pair of outer struts 106'. Thus, support members 120' connect each inner strut 110' to two adjacent outer struts 106'. Likewise, support members 120' connect each outer strut 106' to two adjacent inner struts 110'. Thus, when viewed in the top plan view, inner strut 110', outer struts 106', and support members 120' produce a zigzag pattern. Furthermore, for each adjacent pair of an inner strut 110' and an outer strut 106', a plurality of support members 120' can extend therebetween at a desired orientation, as previously discussed. In view of the foregoing configuration, open column 124' is formed between each adjacent pair of outer struts 106' and comprises the openly exposed area that extends between top outer perimeter rail 24' and bottom outer perimeter rail 84' and is freely exposed to the area outside of fusion implant 10.

In contrast to fusion implant 10, in fusion implant 10' a marking ring 132A and 132B is centrally formed on side wall 44' and side wall 46', respectively. Each marking ring 132 comprises an annular body 134, such as in the form of a ring or tube, that has a passage 136 extending therethrough. In the depicted embodiment, marking rings 132A and 132B are aligned along a common axis and are used for helping determine the position and orientation of fusion implant 10'. That is, once fusion implant is positioned, an X-ray or other imaging can be taken to determine the position of fusion implant 10' relative to the adjacent vertebra. The vertebra and the implant show as white objects in the X-ray. However, open passage 136 shows dark in the X-ray, thereby providing the surgeon a reference point from which the surgeon can more accurately determine the location and/or orientation of fusion implant 10'.

Furthermore, in contrast to fusion implant 10, back wall 42' of fusion implant 10' is not comprised of outer struts 106', inner struts 110' and support members 120'. Rather, back wall 42', as depicted in FIG. 15, comprises a tapered nose. In the depicted embodiment, no openings extend through back wall 42', although openings could be formed extending therethrough. However, because of the intended use of fusion implant 10', back wall 42' is formed as a wedged shaped, tapered nose to permit ease of insertion and positioning of fusion implant 10' between adjacent vertebrae.

The interbody spinal fusion implants of the present invention are typically comprised of medical grade biocompatible metals such as titanium or titanium alloys. Other materials can also be used. The fusion implants are typically formed by using a 3D printing process such as selective laser sintering (SLS), selective laser melting (SLM), or electron beam melting (EBM). Depending on the final design, other manufacturing processes can also be used.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An interbody spinal fusion implant comprising:
   a top wall;
   a bottom wall that is spaced apart from the top wall so that a cavity is formed therebetween;
   a sidewall extending between the top wall and the bottom wall, at least a portion of the sidewall comprising:
   a row of a plurality of spaced apart outer struts, each of the plurality of spaced apart outer struts having a solid body with a length extending between the top wall and the bottom wall, each outer strut having a central longitudinal axis that is linear and extends continuously within a solid portion of the solid body along the length of the outer strut; and
   a row of a plurality of spaced apart inner struts extending between the top wall and the bottom wall, the row of inner struts being set back a distance from the row of outer struts toward the cavity,
   wherein the plurality of outer struts and the plurality of inner struts are linear and wherein the implant can be orientated so that the plurality of outer struts extend vertically in parallel alignment between the top wall and the bottom wall and the inner struts extend vertically between the top wall and the bottom wall in parallel alignment with the outer struts.

2. The interbody spinal fusion implant as recited in claim 1, wherein the inner struts are staggered relative to the outer struts so that each inner strut is disposed between an adjacent pair of outer struts when the row of outer struts are viewed in a front elevational view.

3. The interbody spinal fusion implant as recited in claim 2, wherein each inner strut is centrally disposed between an adjacent pair of outer struts when the row of outer struts are viewed in a front elevational view.

4. The interbody spinal fusion implant as recited in claim 2, wherein each inner strut and the adjacent pair of outer struts each partially bound an open channel having a triangular cross section that extends between the top wall and the bottom wall.

5. The interbody spinal fusion implant as recited in claim 4, wherein each inner strut and the adjacent pair of outer struts are located at corners of the open channel having the triangular cross section that extends between the top wall and the bottom wall.

6. The interbody spinal fusion implant as recited in claim 1, wherein the row of inner struts is linear and the row of outer struts is linear.

7. The interbody spinal fusion implant as recited in claim 1, further comprising a support member extending between one of the plurality of outer struts and one of the plurality of inner struts.

8. The interbody spinal fusion implant as recited in claim 1, wherein the inner struts are spaced apart from and do not directly connect to the outer struts.

9. The interbody spinal fusion implant as recited in claim 1, wherein each of the plurality of spaced apart inner struts has a solid body with a length extending between the top wall and the bottom wall, each inner strut having a central longitudinal axis that is linear and extends continuously within the solid body along the length of the inner strut.

10. The interbody spinal fusion implant as recited in claim 1, wherein each of the plurality of spaced apart outer struts has a transverse cross section that is constant over at least a majority of the length of each outer strut.

11. The interbody spinal fusion implant as recited in claim 1, wherein each of the plurality of spaced apart outer struts comprises a linear rod.

12. An interbody spinal fusion implant comprising:
a top wall comprising a top outer perimeter rail, a top inner perimeter rail that bounds a top access, and a top grating that extends from the top outer perimeter rail to the top inner perimeter rail, wherein the top inner perimeter rail has a length that encircles the top access in a closed loop, at least a portion of the length of the top inner perimeter rail being a rounded curve;
a bottom wall that is spaced apart from the top wall, the bottom wall comprising a bottom outer perimeter rail, a bottom inner perimeter rail that bounds a bottom access, and a bottom grating that extends from the bottom outer perimeter rail to the bottom inner perimeter rail; and
a sidewall extending between the top wall and the bottom wall, at least a portion of the sidewall comprising:
a row of a plurality of spaced apart outer struts extending between the top outer perimeter rail and the bottom outer perimeter rail; and
a row of a plurality of spaced apart inner struts, wherein each of the plurality of spaced apart inner struts has a solid body with a length extending between the top outer perimeter rail and the bottom outer perimeter rail, each inner strut having a central longitudinal axis that is linear and extends continuously within a solid portion of the solid body along the length of the inner strut, the row of inner struts being set back a distance from the row of outer struts toward the top access and the bottom access.

13. The interbody spinal fusion implant as recited in claim 12, wherein the upper grating comprises a network of interconnected rods that bound a plurality of openings.

14. The interbody spinal fusion implant as recited in claim 13, wherein the network of interconnected rods are disposed in a uniform pattern.

15. The interbody spinal fusion implant as recited in claim 13, wherein the rods of the network of interconnected rods interconnect at right angles.

16. The interbody spinal fusion implant as recited in claim 12, wherein the inner struts do not directly connect to the top grating or the bottom grating.

17. The interbody spinal fusion implant as recited in claim 12, wherein the solid body of each inner strut is linear and extend linearly between the top wall and the bottom wall.

18. An interbody spinal fusion implant comprising:
a top wall;
a bottom wall that is spaced apart from the top wall so that a cavity is formed therebetween, the bottom wall comprising:
a bottom outer perimeter rail;
a bottom inner perimeter rail that bounds a bottom access, the bottom access communicating with the cavity; and
a bottom grating that extends from the bottom outer perimeter rail to the bottom inner perimeter rail, the bottom grating comprising a network of interconnected rods that join together at junction nodes and that bound a plurality of openings that communicate with the cavity, each junction node having a bottom surface that faces toward the cavity, the bottom surface of a plurality of the junction nodes being freely exposed so that no structure projects from the bottom surface of the junction node toward the cavity or top wall, the network of interconnected rods comprising a plurality of rods that are linear and that extend linearly between the bottom outer perimeter rail and the bottom inner perimeter rail; and
a sidewall extending between the top wall and the bottom wall, at least a portion of the sidewall comprising a plurality of spaced apart struts extending between the top outer perimeter rail and the bottom outer perimeter rail.

19. The interbody spinal fusion implant as recited in claim 18, wherein the network of interconnected rods are disposed in a uniform pattern.

20. The interbody spinal fusion implant as recited in claim 18, wherein the top wall comprises:
a top outer perimeter rail;
a top inner perimeter rail that bounds a top access, the top access communicating with the cavity; and
a top grating that extends from the top outer perimeter rail to the top inner perimeter rail, the top grating comprising a network of interconnected rods that join together at junction nodes and that bound a plurality of openings that communicate with the cavity, each junction node having a bottom surface that faces toward the cavity, the bottom surface of a plurality of the junction nodes of the top grating being freely exposed.

21. The interbody spinal fusion implant as recited in claim 20, wherein the open cavity extends between the bottom surface of the plurality of the junction nodes of the bottom grating and the bottom surface of the plurality of the junction nodes of the top grating.

22. An interbody spinal fusion implant comprising:
a top wall;
a bottom wall that is spaced apart from the top wall so that a cavity is formed therebetween, the bottom wall comprising:
a bottom outer perimeter rail;
a bottom inner perimeter rail that bounds a bottom access, the bottom access communicating with the cavity; and
a bottom grating that extends from the bottom outer perimeter rail to the bottom inner perimeter rail, the bottom grating comprising a network of interconnected rods that join together at junction nodes and that bound a plurality of openings that communicate with the cavity, a plurality of the junction nodes of the bottom grating comprising a junction body and a tooth projecting from the junction body away from the cavity, the network of interconnected rods comprising a plurality of rods that are linear and that have a solid central core, each of the plurality of rods extending linearly between the bottom outer perimeter rail and the bottom inner perimeter rail; and
a sidewall extending between the top wall and the bottom wall.

23. The interbody spinal fusion implant as recited in claim 22, wherein the junction body has a circular transverse cross section.

24. The interbody spinal fusion implant as recited in claim 22, wherein the tooth has a conical configuration.

25. An interbody spinal fusion implant comprising:
a top wall;
a bottom wall that is spaced apart from the top wall so that a cavity is formed therebetween;
a sidewall extending between the top wall and the bottom wall, at least a portion of the sidewall comprising:
a row of a plurality of spaced apart outer struts extending between the top wall and the bottom wall, the outer struts being linear;
a row of a plurality of spaced apart inner struts extending between the top wall and the bottom wall, the row of inner struts being set back a distance from the row of outer struts toward the cavity, the inner struts being linear,
wherein the inner struts are staggered relative to the outer struts so that each inner strut is disposed between an adjacent pair of outer struts when the row of outer struts are viewed in a front elevational view,
wherein each inner strut and the adjacent pair of outer struts each partially bound an open channel having a triangular cross section that extends between the top wall and the bottom wall, and
wherein the implant can be orientated so that the plurality of outer struts extend vertically in parallel alignment between the top wall and the bottom wall and the inner struts extend vertically between the top wall and the bottom wall in parallel alignment with the outer struts.

26. The interbody spinal fusion implant as recited in claim 25, wherein each inner strut and the adjacent pair of outer struts are located at corners of the open channel having the triangular cross section that extends between the top wall and the bottom wall.

27. An interbody spinal fusion implant comprising:
a top wall;
a bottom wall that is spaced apart from the top wall so that a cavity is formed therebetween;
a sidewall extending between the top wall and the bottom wall, at least a portion of the sidewall comprising:
a row of a plurality of spaced apart outer struts, each of the plurality of spaced apart outer struts being linear and having a solid body with a length extending between the top wall and the bottom wall, each outer strut having a central longitudinal axis that is linear and extends continuously within the solid body along the length of the outer strut, each of the plurality of spaced apart outer struts having a transverse cross section that is constant over at least a majority of the length of each outer strut; and
a row of a plurality of spaced apart inner struts extending between the top wall and the bottom wall, the row of inner struts being set back a distance from the row of outer struts toward the cavity, the inner struts being linear,
wherein the implant can be orientated so that the plurality of outer struts extend vertically in parallel alignment between the top wall and the bottom wall and the inner struts extend vertically between the top wall and the bottom wall in parallel alignment with the outer struts.

\* \* \* \* \*